United States Patent
Ahmed et al.

(10) Patent No.: US 10,548,904 B2
(45) Date of Patent: *Feb. 4, 2020

(54) MONOLITHIC INTRAVAGINAL RINGS COMPRISING PROGESTERONE AND METHODS OF MAKING AND USES THEREOF

(71) Applicant: Ferring B.V., Hoofddorp (NL)

(72) Inventors: Salah U. Ahmed, New City, NY (US); Jiaxiang Tsao, Nanuet, NY (US); Anu Mahashabde, Kendall Park, NJ (US); Diane D. Harrison, Villanova, PA (US)

(73) Assignee: FERRING B.V., Hoofddorp (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/045,311

(22) Filed: Oct. 3, 2013

(65) Prior Publication Data

US 2014/0030311 A1    Jan. 30, 2014

Related U.S. Application Data

(63) Continuation of application No. 12/364,990, filed on Feb. 3, 2009, now Pat. No. 8,580,293.

(60) Provisional application No. 61/026,115, filed on Feb. 4, 2008, provisional application No. 61/139,454, filed on Dec. 19, 2008.

(51) Int. Cl.
| | |
|---|---|
| *A61K 9/00* | (2006.01) |
| *A61K 31/57* | (2006.01) |
| *A61F 6/08* | (2006.01) |
| *A61K 47/34* | (2017.01) |
| *A61K 47/44* | (2017.01) |
| *B29C 45/00* | (2006.01) |
| *B29C 45/72* | (2006.01) |
| *B29K 83/00* | (2006.01) |
| *B29K 105/00* | (2006.01) |
| *B29L 31/00* | (2006.01) |

(52) U.S. Cl.
CPC ............... *A61K 31/57* (2013.01); *A61F 6/08* (2013.01); *A61K 9/0036* (2013.01); *A61K 47/34* (2013.01); *A61K 47/44* (2013.01); *B29C 45/0001* (2013.01); *B29C 45/7207* (2013.01); *B29K 2083/00* (2013.01); *B29K 2105/0035* (2013.01); *B29L 2031/753* (2013.01)

(58) Field of Classification Search
None
See application file for complete search history.

(56) References Cited

U.S. PATENT DOCUMENTS

| | | |
|---|---|---|
| 2,541,137 A | 2/1951 | Warrick |
| 2,723,966 A | 11/1955 | Youngs |
| 2,863,846 A | 12/1958 | Tyler |
| 2,890,188 A | 6/1959 | Konkle et al. |
| 3,022,951 A | 2/1962 | Anderson |
| 3,545,439 A | 12/1970 | Duncan |
| 3,854,480 A | 12/1974 | Zaffaroni |
| 3,948,262 A | 4/1976 | Zaffaroni |
| 4,012,496 A | 3/1977 | Schopflin et al. |
| 4,629,449 A | 12/1986 | Wong |
| 4,816,257 A | 3/1989 | Buster et al. |
| 4,822,616 A | 4/1989 | Zimmerman et al. |
| 4,888,074 A | 12/1989 | Pocknell |
| 5,084,277 A | 1/1992 | Greco et al. |
| 5,116,619 A | 5/1992 | Greco et al. |
| 5,188,835 A | 2/1993 | Lindskog et al. |
| 5,340,585 A | 8/1994 | Pike et al. |
| 5,398,698 A | 3/1995 | Hiller |
| 5,529,782 A | 6/1996 | Staab |
| 5,543,150 A | 8/1996 | Bologna et al. |
| 5,549,913 A | 8/1996 | Colombo et al. |
| 5,694,947 A | 12/1997 | Lehtinen et al. |
| 5,744,463 A | 4/1998 | Bair |
| 5,788,980 A | 8/1998 | Nabahi |
| 5,814,329 A | 9/1998 | Shah |
| 5,869,081 A | 2/1999 | Jackanicz et al. |
| 5,972,372 A | 10/1999 | Saleh et al. |
| 5,985,861 A | 11/1999 | Levine et al. |
| 5,993,856 A | 11/1999 | Ragavan et al. |
| 6,039,968 A | 3/2000 | Nabahi |
| 6,054,447 A | 4/2000 | Levine et al. |
| 6,056,976 A | 5/2000 | Markkula et al. |
| 6,063,395 A | 5/2000 | Markkula et al. |
| 6,086,909 A | 7/2000 | Harrison et al. |
| 6,103,256 A | 8/2000 | Nabahi |
| 6,126,958 A | 10/2000 | Saleh et al. |

(Continued)

FOREIGN PATENT DOCUMENTS

| | | |
|---|---|---|
| JP | H07-002649 A | 1/1995 |
| JP | 2002-518351 | 6/2002 |

(Continued)

OTHER PUBLICATIONS

Bardin, C.W., et al., "The Historic Review of the Clinical Usage of Progesterone and Progestin," *Progesterone and Progestins*, Raven Press, N.Y., 189-202 (1983).

Bulletti, C., et al., "Targeted drug delivery in gynaecology: the first uterine pass effect," *Hum. Reprod.* 12:1073-1079, Oxford University Press, United Kingdom (1997).

(Continued)

*Primary Examiner* — Patricia Duffy
*Assistant Examiner* — Garen Gotfredson
(74) *Attorney, Agent, or Firm* — Foley & Lardner LLP

(57) ABSTRACT

The present invention relates to monolithic intravaginal rings comprising progesterone, methods of making, and uses thereof. The intravaginal rings comprise progesterone, a polysiloxane elastomer, and a pharmaceutically acceptable hydrocarbon or glycerol esters of a fatty acid.

12 Claims, 5 Drawing Sheets

(56) References Cited

U.S. PATENT DOCUMENTS

| | | |
|---|---|---|
| 6,245,757 B1 | 6/2001 | Chopp et al. |
| 6,264,638 B1 | 7/2001 | Contente |
| 6,306,914 B1 | 10/2001 | De Ziegler et al. |
| 6,310,054 B1 | 10/2001 | Rodriguez |
| 6,394,094 B1 | 5/2002 | McKenna et al. |
| 6,416,778 B1 | 7/2002 | Ragavan et al. |
| 6,416,780 B1 | 7/2002 | Passmore et al. |
| 6,511,969 B1 | 1/2003 | Hermsmeyer |
| 6,544,546 B1 | 4/2003 | Groenewegen et al. |
| 6,586,006 B2 | 7/2003 | Roser et al. |
| 6,593,317 B1 | 7/2003 | De Ziegler et al. |
| 6,652,874 B2 | 11/2003 | Ragavan et al. |
| 6,776,164 B2 | 8/2004 | Bunt et al. |
| 7,001,609 B1 | 2/2006 | Matson et al. |
| 7,517,914 B2 | 4/2009 | Richard |
| 7,671,027 B2 | 3/2010 | Loumaye |
| 8,580,293 B2 | 11/2013 | Ahmed et al. |
| 2001/0029357 A1 | 10/2001 | Bunt et al. |
| 2002/0161352 A1 | 10/2002 | Lin et al. |
| 2004/0089308 A1 | 5/2004 | Welch |
| 2004/0151774 A1 | 8/2004 | Pauletti et al. |
| 2004/0265355 A1 | 12/2004 | Shalaby |
| 2005/0042292 A1 | 2/2005 | Muldoon et al. |
| 2005/0197651 A1 | 9/2005 | Chen et al. |
| 2005/0255157 A1 | 11/2005 | Sen et al. |
| 2006/0051391 A1 | 3/2006 | Dvoskin et al. |
| 2006/0052341 A1 | 3/2006 | Cornish et al. |
| 2007/0043332 A1 | 2/2007 | Malcolm et al. |
| 2007/0196433 A1 | 8/2007 | Ron et al. |
| 2007/0243229 A1 | 10/2007 | Smith et al. |
| 2008/0188829 A1 | 8/2008 | Creasy |
| 2008/0199511 A1 | 8/2008 | Sitruk-Ware et al. |
| 2008/0214512 A1 | 9/2008 | Seitz et al. |
| 2008/0233183 A1 | 9/2008 | McCook et al. |
| 2008/0286322 A1 | 11/2008 | Ron et al. |
| 2008/0286339 A1 | 11/2008 | Ron et al. |
| 2009/0137478 A1 | 5/2009 | Bernstein et al. |
| 2009/0306224 A1 | 12/2009 | Gray et al. |
| 2016/0279147 A1 | 9/2016 | Ahmed et al. |

FOREIGN PATENT DOCUMENTS

| | | |
|---|---|---|
| KR | 10-0312764 B1 | 11/2002 |
| WO | WO 1999/65538 | 12/1999 |
| WO | WO2007/128349 A1 | 11/2007 |
| WO | WO2008/140794 | 11/2008 |

OTHER PUBLICATIONS

The International Search Report and the Written Opinion of the International Searching Authority completed for International Application No. PCT/US2009/00672 on Apr. 4, 2009 dated Apr. 17, 2009 (9 pages).

Dragonas C. et al., "Progesterone bioavailability with a progesterone-releasing silicone vaginal ring in IVF candidates", *European Journal of Medical Research*, 12:264-267, 2007.

European Search Report and Written Opinion from European Application No. 10187686, received May 31, 2011.

English translation of technical sheet of the product "Progering", registered at the Chilean Public Health Institute (ISPCH) on Dec. 15, 1998.

Hussain A., et al., "The vagina as a route for systemic drug delivery," *Journal of Controlled Release*, 103:pp. 301-313 (2005).

Landgren, B., et al., "Progesterone Releasing Vaginal Rings for Use in Post Partum Contraception. II Pharmacokinetic Profiles in Women," *Contraception*, 45:343-349 (1992).

Masako Kajihara et al., "Novel Method to Control Release of Lipophilic Drugs with High Potency from Silicone," *Chemical Pharmaceutical Bulletin*, No. 51(I): pp. 11-14 (2003).

Mishell, Jr. et al., "Initial Clinical Studies of Intravaginal Rings Containing Norethindrone and Norgestrel," *Contraception*, 12(3):253-260 (1975).

"Polymer systems technology Limited:"MED-4840, Product Profile, pp. 1-4, XP002639556 (2005).

Smith, K.L., "Membrane Systems: practical applications," *Methods Enzymol*, 112, pp. 504-520 (1985).

Stadtmauer, L. et al., "Pilot study evaluating a progesterone vaginal ring for luteal-phase replacement in donor oocyte recipients," *Fertility and Sterility*, 92(5):1600-1605 (2009), Elsevier for the American Society for Reproductive Medicine, U.S.A. (Available online Nov. 6, 2008, pp. 1-6).

Technical sheet of the product "Progering," registered at the Chilean Public Health Institute (ISPCH) on Dec. 15, 1998.

Toivonen J., "Pituitary and gonadal function during the use of progesterone- or progesterone-estradiol-releasing vaginal rings," *Int. J. Fertil.*, 25(2):106-111 (1980), Allen Press, Inc., Lawrence, Kansas, U.S.A.

Zegers-Hochschild, F. et al., "Prospective randomized trial to evaluate the efficacy of a vaginal ring releasing progesterone for IVF and oocyte donation," *Human Reproduction*, 15(10):22093-2097 (2000), Oxford University Press, England.

Bäckström et al, "Effect of progesterone, administered via intravaginal rings, on serum concentrations of oestradiol, FSH, LH and prolactin in women", J. Reprod. Fert. (1982) 64, p. 53-58.

Massai et al, "Vaginal rings for contraception in lactating women", Steroid 65 (2000) 703-707.

Geber, S. et al, "Comparison between two forms of vaginally administered progesterone for luteal phase support in assisted reproduction cycles", Reproductive BioMedicine Online, vol. 14, No. 2, 2007, p. 155-158.

International Preliminary Report on Patentability in Application No. PCT/US2009/00672 dated Mar. 23, 2011.

Noyes et al., "Dating the endometrial biopsy," Fertility and Sterility, 1:3- 25 (1950).

Penzias, A.S., "Luteal phase support," Fertility and Sterility, 77:318-323 (2002).

Pritts et al., "Luteal phase support in infertility treatment: a meta-analysis of the randomized trials," Human Reproduction 17:2287-2299 (2002).

Soliman et al., "The role of luteal phase support in infertility treatment: a meta-analysis of randomized trials," Fertility and Sterility vol. 61, pp. 1068-1076 (1994).

Toner, J. P., "Vaginal delivery of progesterone in donor oocyte therapy," Human Reproduction vol. 15(Suppl. 1), pp. 166-171 (2000).

| Time (day) | Amount Released (mg/day) | %RSD |
|---|---|---|
| 1 | 23.8 | 5.5 |
| 2 | 22.8 | 6.0 |
| 3 | 20.2 | 9.7 |
| 4 | 19.5 | 9.2 |
| 5 | 20.4 | 9.2 |
| 6 | 19.1 | 7.4 |
| 7 | 19.2 | 9.9 |

MONOLITHIC INTRAVAGINAL RINGS COMPRISING PROGESTERONE AND METHODS OF MAKING AND USES THEREOF

This application claims benefit of the filing dates of U.S. Appl. No. 61/026,115, filed Feb. 4, 2008, and U.S. Appl. No. 61/139,454, filed Dec. 19, 2008, each of which is hereby incorporated by reference in its entirety.

FIELD OF THE INVENTION

The present invention relates to monolithic intravaginal rings comprising progesterone, methods of making, and uses thereof. The intravaginal rings comprise progesterone, a polysiloxane elastomer, and a pharmaceutically acceptable hydrocarbon or glycerol esters of a fatty acid.

BACKGROUND OF THE INVENTION

Progesterone is a C-21 steroid hormone and belongs to a class of hormones called progestogens. It is the major naturally occurring steroid and is a precursor in the biosynthesis of other steroids, particularly glucocorticoids, androgens and estrogens.

Progesterone stimulates the growth of the uterus and also stimulates a number of specific changes in the endometrium and myometrium. Progesterone is essential for the development of decidual tissue and the differentiation of luminal and glandular epithelial tissue. It also plays several roles in gestation, including breast enlargement, inhibition of uterine contractility, maintenance of gestation, immunological protection of the embryo, and inhibition of prostaglandin synthesis.

Progesterone has been used in the treatment of a number of clinical disorders such as luteal phase defects, dysfunctional uterine bleeding, endometriosis, endometrial carcinoma, benign breast disease, pre-eclampsia, and regimens of in vitro fertilization. The luteal phase of a natural cycle is characterized by the formation of a corpus luteum, which secretes steroid hormones, including progesterone. After fertilization and implantation, the developing blastocyst secretes human chorionic gonadotropin ("hCG"), which maintains the corpus luteum and its secretions. Normal luteal function is essential for maintaining pregnancy and data suggest that progesterone is necessary for the maintenance of early pregnancy. Penzias, A. S., *Fertility and Sterility* 77:318-323 (2002).

Unfortunately, not all women of reproductive age are able to become pregnant, or maintain a pregnancy; indeed, about twelve to fifteen percent of women of reproductive age in the United States have received an infertility service at some time in their lives. Assisted Reproductive Technology ("ART") generally involves the surgical removal of eggs from a woman's ovaries, fertilizing them with sperm in the laboratory, and then returning them to either the donor woman's or another woman's uterus (Centers for Disease Control, Assisted Reproductive Technology Success Rates, National Summary and Fertility Clinic Reports. U.S. Department of Health and Human Services, 2004). There are three types of ART: (a) IVF (in vitro fertilization) involves extracting the eggs, fertilizing them in the laboratory, and transferring resulting embryos to the uterus through the cervix, (b) GIFT (gamete intrafallopian transfer) involves placing unfertilized eggs and sperm into the woman's fallopian tubes using a laparoscope through an abdominal incision, and (c) ZIFT (zygote intrafallopian transfer) involves extracting the eggs, fertilizing them in the laboratory, and using a laparoscope to place the fertilized egg(s) into a woman's fallopian tubes.

ART is also further classified by whether a woman's own eggs were used (nondonor), or eggs were donated from another woman (donor). In addition, the embryos used can be newly fertilized (fresh), or previously fertilized, frozen, and then thawed (frozen). For many women, in conjunction with ART, steps must be taken to prime the uterus for implantation, and to sustain the pregnancy after implantation. There have been many tools developed to aid in this process.

In the mid-1980s, gonadotrophin releasing hormone ("GnRH") agonists were incorporated into ovarian stimulation regimens and are associated with improved outcomes after IVF and other assisted reproductive technologies. GnRH agonists work by suppressing the pituitary and preventing premature surges of endogenous luteinizing hormone ("LH") during IVF cycles, allowing time for a larger number of oocytes to reach maturity prior to harvesting as well as increasing follicular growth. However, GnRH agonists inhibit the corpora lutea in these cycles and may create an iatrogenic luteal phase defect.

Use of a GnRH agonist causes suppression of pituitary LH secretion for as long as 10 days after the last dose and pituitary function may not return completely until 2-3 weeks after the end of therapy. Without this LH signal, the corpus luteum may be dysfunctional, and subsequent progesterone and estrogen secretion may be abnormal, compromising endometrial receptivity, and potentially leading to decreased implantation and pregnancy rates. Pritts et al., *Human Reproduction* 17:2287-2299 (2002).

Various hormones, including estrogens, progesterone, and hCG, have been used during the luteal phase and beyond in IVF cycles for luteal phase support. A 1994 meta-analysis showed that the use of hCG or progesterone led to significantly higher pregnancy rates than placebo. Soliman et al., *Fertility and Sterility* 61:1068-76 (1994). Progesterone in numerous forms (oral, vaginal, intramuscular ("IM")) is considered to be the agent of choice because hCG is associated with a higher risk of ovarian hyperstimulation syndrome ("OHSS"), a potentially life-threatening condition associated with an increased risk of thromboembolism.

Most treatment protocols advocate the use of progesterone throughout the first trimester of pregnancy, since corpus luteum activity has been demonstrated up to week 10 of pregnancy, although progesterone supplementation continuing beyond a positive serum pregnancy test may not be needed. The goal of progesterone supplementation is therefore to assist a corpus luteum that may have become compromised during ovulation induction or oocyte retrieval.

Oral, IM, and intravaginal progesterone preparations are available. Oral formulations appear to be inferior for luteal support. Serum progesterone levels are highest with IM administration, but because of the uterine first pass effect with IM administration, vaginal administration results in higher endometrial progesterone levels. Bulletti et al., *Human Reproduction* 12:1073-9 (1997).

IM progesterone (50-100 mg daily) is widely used, but requires daily injections and is painful, uncomfortable, and inconvenient for patients; some patients may even develop a sterile abscess or an allergic response to the oil vehicle. Toner J. P., *Human Reproduction* 15 Supp. 1:166-71 (2000). Vaginal progesterone gel (Crinone®/Prochieve® 8%; Columbia Laboratories, Livingston, N.J.) is less painful and easier to use than IM, but also requires daily dosing, may be messy, and due to potential leakage, may not provide a full dose with every application. Crinone® is a bioadhesive vaginal gel containing micronized progesterone in an emulsion system. The carrier vehicle is an oil in water emulsion containing the water swellable, but insoluble, polymer polycarbophil.

The use of a progesterone vaginal insert (Endometrin®) 3 times daily has recently been approved by the U.S. Food and Drug Administration ("FDA") to support embryo implantation and early pregnancy by supplementation of corpus luteal function as part of an ART treatment program for infertile women. In addition, vaginal use multiple times daily of micronized progesterone capsules has been reported and is used clinically, but luteal phase supplementation or replacement is not an FDA-approved indication for this product.

There is also published information comparing a vaginal progesterone ring to IM progesterone for use in both IVF and oocyte donation. Zegers-Hochschild et al., *Human Reproduction* 15:2093-2097 (2000).

Intravaginal devices for delivering progesterone and/or intravaginal devices comprising polysiloxane elastomers are discussed in U.S. Pat. Nos. 3,545,439; 3,948,262; 4,012,496; 5,869,081; 6,103,256; 6,056,976; and 6,063,395.

BRIEF SUMMARY OF THE INVENTION

The present invention is directed to a method for treating a luteal phase defect in a patient in need thereof, the method comprising administering to the patient a monolithic intravaginal ring comprising (a) a therapeutically effective amount of progesterone, (b) a polysiloxane elastomer, and (c) a pharmaceutically acceptable hydrocarbon or glycerol esters of a fatty acid, wherein the polysiloxane elastomer is present in a concentration of about 55% to about 90% by total weight of the ring.

The present invention is directed to a method for treating a luteal phase defect in a patient in need thereof, the method comprising administering to the patient a monolithic intravaginal ring comprising (a) a therapeutically effective amount of progesterone, (b) a polysiloxane elastomer, and (c) a pharmaceutically acceptable oil, wherein the polysiloxane elastomer is present in a concentration of about 55% to about 90% by total weight of the ring.

The present invention is directed to a monolithic intravaginal ring for treating a luteal phase defect in a patient in need thereof, the ring comprising (a) about 5% to about 40% by weight of progesterone, (b) about 55% to about 90% by weight of polysiloxane elastomer, and (c) about 0.1% to about 10% by weight of a pharmaceutically acceptable hydrocarbon or glycerol esters of a fatty acid, wherein the progesterone is homogeneously dispersed in the elastomer.

The present invention is directed to a monolithic intravaginal ring for treating a luteal phase defect in a patient in need thereof the ring comprising (a) about 5% to about 40% by weight of progesterone, (b) about 55% to about 90% by weight of polysiloxane elastomer, and (c) about 0.1% to about 10% by weight of a pharmaceutically acceptable oil, wherein the progesterone is homogeneously dispersed in the elastomer.

The present invention is directed to a process for making a monolithic intravaginal ring, the process comprising (a) mixing progesterone, a pharmaceutically acceptable hydrocarbon or glycerol esters of a fatty acid, and a polysiloxane to form a homogeneous mixture, (b) placing the homogeneous mixture into a mold, and (c) curing the mold at about 60° C. to about 180° C., wherein the polysiloxane is present in a concentration of about 55% to about 90% by total weight of the ring.

The present invention is directed to a process for making a monolithic intravaginal ring, the process comprising (a) mixing progesterone, a pharmaceutically acceptable oil, and a polysiloxane to form a homogeneous mixture, and (b) placing the homogeneous mixture into a mold, wherein the polysiloxane is present in a concentration of about 55% to about 90% by total weight of the ring.

The present invention is directed to a method for treating a luteal phase defect in a patient in need thereof, the method comprising administering to a patient a monolithic intravaginal ring comprising (a) progesterone, (b) a dimethylpolysiloxane elastomer, and (c) a pharmaceutically acceptable hydrocarbon or glycerol esters of a fatty acid, wherein the ratio of progesterone to elastomer is about 1:1 to about 1:10, the progesterone is homogeneously dispersed in the elastomer, the ratio of progesterone to hydrocarbon or glycerol esters of a fatty acid is about 1:0.1 to about 1:100, and wherein the progesterone is released from the monolithic intravaginal ring for up to about 18 days after administration to the patient.

The present invention is directed to a method for treating a luteal phase defect in a patient in need thereof, the method comprising administering to a patient a monolithic intravaginal ring comprising (a) progesterone, (b) a dimethylpolysiloxane elastomer, and (c) a pharmaceutically acceptable oil, in a ratio of about 4:15:1, respectively, wherein the progesterone is homogeneously dispersed in the elastomer, and wherein the progesterone is released from the monolithic intravaginal ring for up to about 18 days after administration to the patient.

The present invention is directed to a method for treating a luteal phase defect in a patient in need thereof, the method comprising administering to the patient a monolithic intravaginal ring comprising (a) about 15% to about 25% by weight of progesterone, (b) about 70% to about 80% by weight of a dimethylpolysiloxane elastomer, and (c) about 1% to about 10% by weight of a pharmaceutically acceptable hydrocarbon or glycerol esters of a fatty acid, wherein the progesterone is homogeneously dispersed in the elastomer, and wherein the progesterone is released from the monolithic intravaginal ring for up to about 18 days after administration to the patient.

The present invention is directed to a method for treating a luteal phase defect in a patient in need thereof, the method comprising administering to the patient a monolithic intravaginal ring comprising (a) about 15% to about 25% by weight of progesterone, (b) about 70% to about 80% by weight of a dimethylpolysiloxane elastomer, and (c) about 1% to about 10% by weight of a pharmaceutically acceptable oil, wherein the progesterone is homogeneously dispersed in the elastomer, and wherein the progesterone is released from the monolithic intravaginal ring for up to about 18 days after administration to the patient.

The present invention is directed to a method for treating a luteal phase defect in a patient in need thereof, the method comprising administering to the patient a monolithic intravaginal ring comprising (a) progesterone, (b) a dimethylpolysiloxane elastomer, and (c) mineral oil, in a ratio of about 4:15:1, respectively, wherein the progesterone is homogeneously dispersed in the elastomer, and released from the intravaginal ring at about 15 mg/day to about 25 mg/day in vivo and wherein the intravaginal ring is replaced after about every 7 days following administration to the patient.

The present invention is directed to a method for treating a luteal phase defect in a patient in need thereof, the method comprising administering to the patient a monolithic intravaginal ring comprising (a) about 20% progesterone, (b) about 75% MED-4840, and (c) about 5% mineral oil, wherein the progesterone is homogeneously dispersed in the elastomer, and released from the intravaginal ring at about 15 mg/day to about 25 mg/day in vivo and wherein the intravaginal ring is replaced after about every 7 days following administration to the patient.

In some embodiments, the progesterone is homogeneously dispersed in the polysiloxane elastomer.

In some embodiments, the polysiloxane elastomer is a diorganopolysiloxane elastomer. The diorganopolysiloxane elastomer can be a dimethylpolysiloxane elastomer. The dimethylpolysiloxane elastomer can further comprise a dimethylmethylhydrogen polysiloxane crosslink.

In some embodiments, the pharmaceutically acceptable hydrocarbon or glycerol esters of a fatty acid is present in a concentration of about 0.1% to about 10% by total weight of the ring.

In some embodiments, the pharmaceutically acceptable hydrocarbon or glycerol esters of a fatty acid is selected from mineral oil, silicone oil and combinations thereof. In some embodiments, the pharmaceutically acceptable hydrocarbon or glycerol esters of a fatty acid is mineral oil.

In some embodiments, the progesterone is present in a concentration of about 15% to about 30% by total weight of the ring.

In some embodiments, the progesterone is released at a steady rate for about 1 day to about 14 days. In some embodiments, the progesterone is released at a steady rate for about 1 day to about 10 days. In some embodiments, the progesterone is released at a steady rate for about 1 day to about 7 days.

In some embodiments, the progesterone is released from the monolithic intravaginal ring at a steady rate for up to about 10 days after administration to the patient. In some embodiments, the progesterone is released from the monolithic intravaginal ring at a steady rate for up to about 14 days after administration to the patient. In some embodiments, the progesterone is released from the monolithic intravaginal ring at a steady rate for up to about 18 days after administration to the patient.

In some embodiments, the polysiloxane is vinyl end blocked. In some embodiments, the polysiloxane is dimethylpolysiloxane.

In some embodiments, the process further comprises mixing a second polysiloxane into the homogeneous mixture prior to placing into the mold. In some embodiments, the second polysiloxane is a crosslinker. In some embodiments, the crosslinker is dimethylmethylhydrogen polysiloxane.

In some embodiments, the placing of the homogeneous mixture is by injection.

In some embodiments, the progesterone is released from the intravaginal ring at about 10 mg/day to about 40 mg/day in vivo. In some embodiments, the progesterone is released from the intravaginal ring at about 10 mg/day to about 30 mg/day in vivo. In some embodiments, the progesterone is released from the intravaginal ring at about 15 mg/day to about 25 mg/day in vivo.

In some embodiments, the intravaginal ring is replaced after about 14 days following administration to the patient.

In some embodiments, the intravaginal ring is replaced after about 7 days following administration to the patient.

DETAILED DESCRIPTION OF THE INVENTION

Figure 1:
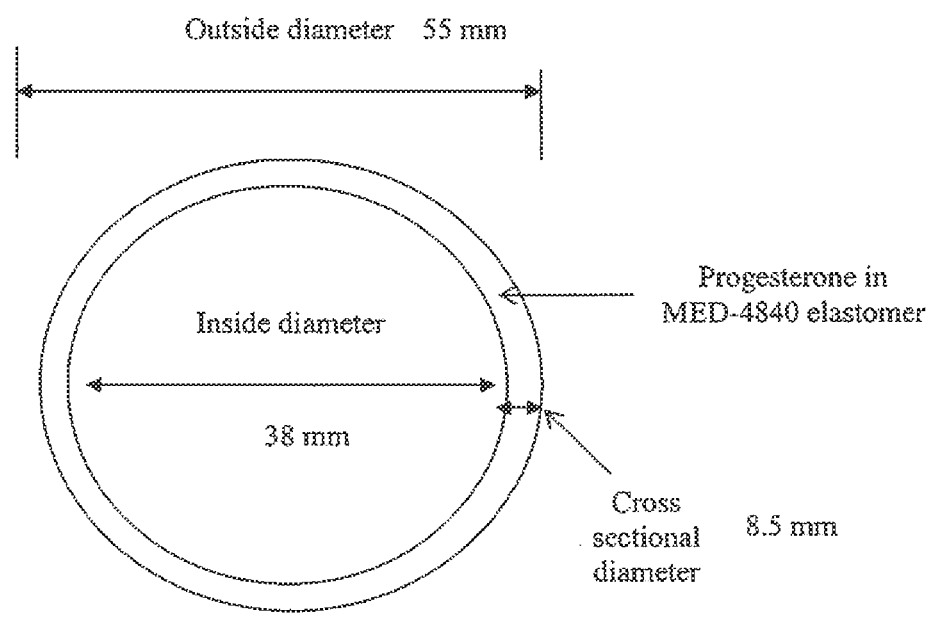
FIG. 1 depicts a top-down view of a monolithic intravaginal ring of the present invention.

The present invention relates to monolithic intravaginal rings comprising progesterone, methods of making, and uses thereof. The intravaginal rings comprise progesterone, a polysiloxane elastomer, and a pharmaceutically acceptable hydrocarbon or glycerol esters of a fatty acid.

Throughout the present disclosure, all expressions of percentage, ratio, and the like are "by weight" unless otherwise indicated. As used herein, "by weight" is synonymous with the term "by mass," and indicates that a ratio or percentage defined herein is done according to weight rather than volume, thickness, or some other measure.

As used herein, the term "about," when used in conjunction with a percentage or other numerical amount, means plus or minus 10% of that percentage or other numerical amount. For example, the term "about 80%," would encompass 80% plus or minus 8%.

The present invention is directed to a method for treating a luteal phase defect in a patient in need thereof, the method comprising administering to the patient a monolithic intravaginal ring comprising (a) a therapeutically effective amount of progesterone, (b) a polysiloxane elastomer, and (c) a pharmaceutically acceptable hydrocarbon or glycerol esters of a fatty acid.

The term "therapeutically effective amount" refers to an amount of the pharmaceutical composition (i.e., progesterone) that treats a condition, disorder, or disease in a subject. The precise therapeutic dosage of progesterone necessary to be therapeutically effective can vary between subjects (e.g., due to age, body weight, sex, condition of the subject, the nature and severity of the disorder or disease to be treated, and the like). Thus, the therapeutically effective amount cannot always be specified in advance, but can be determined by a caregiver, for example, by a physician using dose titration. Appropriate dosage amounts can also be determined by routine experimentation with animal models.

The terms "treat" and "treatment" refer to both therapeutic treatment and prophylactic or preventative measures, wherein the object is to prevent or slow down (lessen) an undesired physiological condition, disorder or disease, or obtain beneficial or desired clinical results. For purposes of this invention, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state, whether detectable or undetectable; or enhancement or improvement of condition, disorder or disease. Treatment includes eliciting a clinically significant response, without excessive levels of side effects.

The term "luteal phase defect" refers to a disruption in the normal female menstrual cycle. The defect occurs when the female body does not produce enough of the hormone progesterone. This results in a delay in the development of the lining of the uterus (endometrium) during the luteal phase. The luteal phase is defined as the time between ovulation and the start of the next menstrual cycle. Luteal phase defects can result in the inability to sustain a pregnancy, whereby the uterine lining begins to break down, bringing on menstrual bleeding and causing miscarriage.

The present invention is directed to a method for treating a luteal phase defect in a patient in need thereof, the method comprising administering to the patient a monolithic intravaginal ring comprising (a) a therapeutically effective amount of progesterone, (b) a polysiloxane elastomer, and (c) a pharmaceutically acceptable hydrocarbon or glycerol esters of a fatty acid, wherein the polysiloxane elastomer is present in a concentration of about 55% to about 90% by total weight of the ring.

The present invention is also directed to a method for treating a luteal phase defect in a patient in need thereof; the method comprising administering to the patient a monolithic intravaginal ring comprising (a) a therapeutically effective amount of progesterone, (b) a polysiloxane elastomer, and (c) a pharmaceutically acceptable oil, wherein the polysiloxane elastomer is present in a concentration of about 55% to about 90% by total weight of the ring.

The monolithic intravaginal ring of the present invention can be useful as part of an assisted reproductive technology (ART) treatment for infertile women with progesterone deficiency. The monolithic intravaginal ring of the present invention can be useful for luteal phase supplementation or replacement, e.g., partial luteal support for in vitro fertilization or complete luteal support for oocyte donation. The monolithic intravaginal ring of the present invention can also be useful for the treatment of secondary amenorrhea.

The term "monolithic intravaginal ring" refers to a ring that is a matrix ring, wherein the matrix ring does not comprise a membrane or wall that encloses a reservoir.

The intravaginal ring provides for administration or application of an active agent to the vaginal and/or urogenital tract of a subject, including, e.g., the vagina, cervix, or uterus of a female. In some embodiments, the intravaginal ring is annular in shape. As used herein, "annular" refers to a shape of, relating to, or forming a ring. Annular shapes suitable for use with the present invention include a ring, an oval, an ellipse, a toroid, and the like.

The intravaginal ring of the present invention can be flexible. As used herein, "flexible" refers to the ability of a solid or semi-solid to bend or withstand stress and strain without being damaged or broken. For example, the intravaginal ring of the present invention can be deformed or flexed, such as, for example, using finger pressure (e.g., applying pressure from opposite external sides of the device using the fingers), and upon removal of the pressure, return to its original shape. The flexible properties of the intravaginal ring of the present invention are useful for enhancing user comfort, and also for ease of administration to the vaginal tract and/or removal of the device from the vaginal tract.

The intravaginal ring of the present invention can be any size suitable for placement in a vaginal tract. In some embodiments, the outside diameter of the ring is about 35 mm to about 65 mm, about 40 mm to about 60 mm, or about 45 mm to about 55 mm. In some embodiments, the outside diameter of the ring is about 55 mm. As used herein, an "outside diameter" refers to any straight line segment that passes through the center of the ring and whose endpoints are on the outer perimeter of the ring, see, e.g., FIG. 1.

In some embodiments, the inside diameter of the ring is about 25 mm to about 45 mm, or about 30 mm to about 40 mm. In some embodiments, the inside diameter of the ring is about 38 mm. As used herein, an "inside diameter" refers to any straight line segment that passes through the center of the ring and whose endpoints are on the inner perimeter of the ring, see, e.g., FIG. 1.

In some embodiments, the cross-sectional diameter of the ring is about 5 mm to about 15 mm, or about 7 mm to about 10 mm. In some embodiments, the cross-sectional diameter is about 8.5 mm. As used herein, a "cross-sectional diameter" refers to any straight line segment whose endpoints are on the inner and outer perimeter of the ring, see, e.g., FIG. 1.

In some embodiments, the monolithic intravaginal ring of the present invention comprises progesterone (pregn-4-ene-3,20-dione), as illustrated in Formula I.

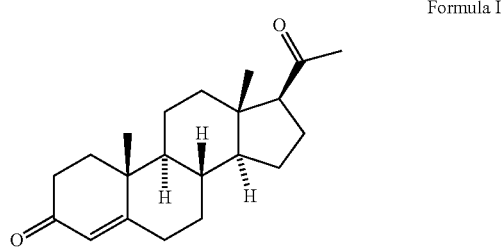

Formula I

In some embodiments, the progesterone can be micronized. As used herein, "micronized" refers to particles of a composition that have been reduced to micron size.

As used herein, the term "particle size" refers to particle diameter. Particle size and particle size distribution can be measured using, for example, a Hyac/Royco particle size analyzer, a Malvern particle size analyzer, a Beckman Coulter laser diffraction particle size analyzer, a Shimadzu laser diffraction particle size analyzer, or any other particle size measurement apparatus or technique known to persons of ordinary skill in the art. As used herein, the term "particle diameter" relates to a volumetric measurement based on an approximate spherical shape of a particle. The present invention can also comprise semi-spherical, ellipsoidal, or cylindrical particles without limitation. In addition to encompassing progesterone particles of a given size, the present invention is also directed to compositions wherein the distribution of particle sizes of progesterone and excipients is controlled. As used herein, a "distribution" refers to the number or concentration (i.e., percentage) of particles having a certain size, or range of sizes, within a given lot, batch, or dosage form of the present invention.

Materials used in the intravaginal ring of the present invention are suitable for placement in the vaginal tract, i.e., they are nontoxic and can further be non-absorbable in the subject. In some embodiments, the materials are compatible with an active agent. In some embodiments, the materials can be capable of being suitably shaped for intravaginal administration.

In some embodiments, the intravaginal ring comprises a polymer material that is an elastomer, e.g., a thermosetting elastomer, including, e.g., a silicone co-polymer (thermosetting type). For example, the intravaginal ring of the present invention can be produced using silicone polymers which can include various catalysts or cross-linking agents. Such silicone compounds, catalysts and cross-linking agents are known in the art, see e.g., U.S. Pat. No. 4,888,074. A silicone composition can include any organo-silicone compound capable of cross-linking, with or without the presence of cross-linking agents.

As used herein, an "elastomer" refers to an amorphous polymer network formed when a polymer or a mixture of polymers undergo cross-linking. Each polymer is comprised of monomeric units, which are linked together to form the polymer. The monomeric units can comprise carbon, hydrogen, oxygen, silicon, halogen, or a combination thereof.

In some embodiments, the intravaginal ring comprises a polysiloxane. As used herein, a "polysiloxane" refers to any of various compounds containing alternate silicon and oxygen atoms in either a linear or cyclic arrangement usually with one or two organic groups attached to each silicon atom. For example, polysiloxanes include substituted polysiloxanes, and diorganopolysiloxanes such as diarylpolysiloxanes and dialkylpolysiloxanes; an example of the latter is dimethylpolysiloxane, as illustrated in Formula II.

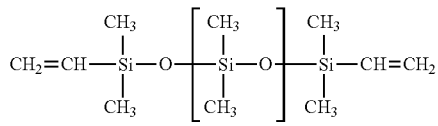

Formula II

Such dimethylpolysiloxane polymers can be thermoset to the corresponding elastomer by vulcanization with peroxide curing catalysts, e.g., benzoyl peroxide or di-p-chlorobenzoyl peroxide at temperatures of about 200° C. and requiring additional heat after treatment as described in U.S. Pat. Nos. 2,541,137; 2,723,966; 2,863,846; 2,890,188; and 3,022,951.

An example of a two-component dimethylpolysiloxane composition, which is platinum-catalyzed at room temperature or under slightly elevated temperature and capable of cross-linking, is MED-4840 (NuSil Technology LLC, Carpinteria, Calif.). In some embodiments of the present invention, a monolithic intravaginal ring can comprise progesterone, mineral oil and MED-4840 elastomer. The MED-4840 elastomer is composed of two parts, part A and part B. The chemical composition of MED-4840 part A comprises dimethylpolysiloxane vinyl endblocked polymer, fumed silica (non-crystalline) trimethylsilyl treated and a platinum silicone complex. The chemical composition of MED-4840 part B comprises a dimethylpolysiloxane vinyl endblocked polymer, fumed silica (non-crystalline) trimethylsilyl treated, dimethylmethylhydrogen polysiloxane and 2-methyl-3-butyn-2-ol. Form A and form B undergo cross-linkage to form a dimethylpolysiloxane elastomer.

In some embodiments of the present invention, the polysiloxane elastomer is a diorganopolysiloxane elastomer. In some embodiments, the diorganopolysiloxane elastomer is dimethylpolysiloxane elastomer. In some embodiments, the dimethylpolysiloxane elastomer further comprises a dimethylmethylhydrogen polysiloxane cross-link. In some embodiments of the present invention, the polysiloxane elastomer is MED-4840.

In some embodiments, the polysiloxane elastomer is present in a concentration of about 55% to about 90% by total weight of the ring. In some embodiments, the polysiloxane elastomer is present in a concentration of about 60% to about 80% by total weight of the ring, or about 65% to about 75% by total weight of the ring.

In some embodiments, the monolithic intravaginal ring comprises a pharmaceutically-acceptable hydrocarbon or glycerol esters of a fatty acid. The glycerol esters of a fatty acid can be monoesters, diesters, triesters and mixtures thereof. The fatty acid glycerol esters can be of a synthetic or natural origin. In some embodiments, the monolithic intravaginal ring comprises a pharmaceutically-acceptable oil. In some embodiments the oil can be a vegetable oil or a mineral oil. In some embodiments, the oil can be olive oil, peanut oil, lanoline, silicone oil, mineral oil, glycerine fatty acids or combinations thereof.

In some embodiments, the pharmaceutically acceptable hydrocarbon or glycerol esters of a fatty acid is present in a concentration of about 0.1% to about 10% by total weight of the ring. In some embodiments the pharmaceutically acceptable hydrocarbon or glycerol esters of a fatty acid is present in a concentration of about 1% to about 6% by total weight of the ring. In some embodiments of the present invention, the pharmaceutically acceptable hydrocarbon or glycerol esters of a fatty acid is mineral oil.

In some embodiments, progesterone is substantially homogeneously dispersed in the intravaginal ring. As used herein, "homogeneous" refers to a composition, e.g., the intravaginal ring, that has a substantially uniform distribution of ingredients throughout (i.e., an intravaginal ring of the present invention does not have a composition gradient, or a multi-laminate structure).

In some embodiments, the progesterone is present in a concentration of about 1% to about 60% by total weight of the ring, in a concentration of about 10% to about 40% by total weight of the ring, in a concentration of about 15% to about 30% by total weight of the ring, or in a concentration of about 20% to about 25% by total weight of the ring.

In some embodiments, the intravaginal rings of the present invention release about 10 mg to about 50 mg of progesterone/day in vitro, about 10 mg to about 40 mg of progesterone/day in vitro, about 10 mg to about 30 mg of progesterone/day in vitro, or about 10 mg to about 20 mg of progesterone/day in vitro.

In some embodiments, the intravaginal rings release about 14 mg to about 28 mg of progesterone/day in vitro, about 16 mg to about 25 mg of progesterone/day in vitro, or about 18 mg to about 22 mg of progesterone/day in vitro. In some embodiments, the intravaginal ring releases about 16 mg of progesterone/day in vitro. In some embodiments, the intravaginal ring releases about 19 mg of progesterone/day in vitro.

In some embodiments, the intravaginal rings release about 25 mg to about 50 mg of progesterone/day in vitro, about 25 mg to about 40 mg of progesterone/day in vitro, about 30 mg to about 40 mg of progesterone/day in vitro, or about 32 mg to about 36 mg of progesterone/day in vitro.

As used herein, the "rate of release" or "release rate" refers to an amount or concentration of active agent that is released from the intravaginal ring over a defined period of time. The release rate can be measured in vitro by placing the ring into an Orbital shaker at 50 rpm containing 250 mL of 0.008 M SDS at 37° C. The active agent can be assayed by methods known in the art, e.g., by HPLC.

The intravaginal rings of the present invention can release about 10 mg to about 40 mg of progesterone/day in vivo, about 10 mg to about 30 mg of progesterone/day in vivo, about 10 mg to about 25 mg of progesterone/day in vivo, about 12 mg to about 25 mg of progesterone/day in vivo, about 15 mg to about 25 mg of progesterone/day in vivo, about 16 mg to about 24 mg of progesterone/day in vivo, about 17 mg to about 22 mg of progesterone/day in vivo, or about 18 mg to about 22 mg of progesterone/day in vivo.

In some embodiments, the progesterone is released from the intravaginal ring at a steady rate for up to about 18 days after administration to a patient, for up to about 14 days after administration to a patient, for up to about 7 days after administration to a patient, or for up to about 4 days after administration to a patient.

In some embodiments, after the first day of administration to a patient, the progesterone is released at a steady rate for up to about 17 additional days, for up to about 13 additional days, for up to about 6 additional days, or for up to about 3 additional days after administration.

As used herein, a "steady rate" is a release rate that does not vary by an amount greater than about 70% of the amount of progesterone released in vivo per day, by an amount greater than about 60% of the amount of progesterone released in vivo per day, by an amount greater than about 50% of the amount of progesterone released in vivo per day, by an amount greater than about 40% of the amount of progesterone released in vivo per day, by an amount greater than about 30% of the amount of progesterone released in vivo per day, by an amount greater than about 20% of the amount of progesterone released in vivo per day, by an amount greater than about 10% of the amount of progesterone released in vivo per day, or by an amount greater than about 5% of the amount of progesterone released in vivo per day.

In some embodiments, the steady rate encompasses a release rate in vivo of about 15 mg/day to about 25 mg/day, about 16 mg/day to about 24 mg/day, about 17 mg/day to about 22 mg/day or about 18 mg/day to about 20 mg/day. In some embodiments, the steady rate encompasses a release rate of about 12 mg/day to about 16 mg/day, about 12 mg/day to about 15 mg/day, about 12 mg/day to about 14 mg/day, or about 12 mg/day to about 13 mg/day. In some embodiments, the steady rate encompasses about 13 mg/day to about 18 mg/day, about 13 mg/day to about 17 mg/day, about 13 mg/day to about 16 mg/day, about 13 mg/day to about 15 mg/day, or about 13 mg/day to about 14 mg/day. In some embodiments, the steady rate encompasses about 11 mg/day to about 15 mg/day, about 11 mg/day to about 14 mg/day, about 11 mg/day to about 13 mg/day, or about 11 mg/day to about 12 mg/day.

In some embodiments, the serum levels of progesterone are maintained over a relatively constant level. In some embodiments, serum progesterone levels are maintained at about 1 ng/mL to about 10 ng/mL, about 2 ng/mL to about 8 ng/mL, about 2 ng/mL to about 7 ng/mL, about 2 ng/mL to about 6 ng/mL, about 3 ng/mL to about 6 ng/mL, about 4 ng/mL to about 6 ng/mL, or about 5 ng/mL to about 6 ng/mL.

In some embodiments, serum progesterone levels are maintained at about 4 ng/mL to about 10 ng/mL, about 4 ng/mL to about 9 ng/mL, about 5 ng/mL to about 8 ng/mL, or about 6 ng/mL to about 8 ng/mL.

In some embodiments, progesterone serum levels are maintained below about 7 ng/mL, below about 6 ng/mL, below about 5 ng/mL, below about 4 ng/mL, below about 3 ng/mL, below about 2 ng/mL, or below about 1 ng/mL.

In some embodiments, these progesterone serum levels are maintained from about 1 day to about 18 days after administration to a patient, from about 1 day to about 14 days after administration to a patient, from about 1 day to about 10 days after administration to a patient, from about 1 day to about 7 days after administration to a patient, or from about 1 day to about 4 days after administration to a patient. In some embodiments, these progesterone serum levels are maintained from about 2 days to about 18 days after administration to a patient, from about 2 days to about 14 days after administration to a patient, from about 2 days to about 7 days after administration to a patient, or from about 2 days to about 4 days after administration to a patient.

In some embodiments, the present invention is directed to a monolithic intravaginal ring for treating a luteal phase defect in a patient in need thereof, the ring comprising about 5% to about 40% by weight of progesterone, about 55% to about 90% by weight of polysiloxane elastomer, and about 0.1% to about 10% by weight of a pharmaceutically acceptable hydrocarbon or glycerol esters of a fatty acid, wherein the progesterone is homogeneously dispersed in the elastomer.

In some embodiments, the present invention is directed to a monolithic intravaginal ring for treating a luteal phase defect in a patient in need thereof, the ring comprising about 5% to about 40% by weight of progesterone, about 55% to about 90% by weight of dimethylpolysiloxane elastomer, and about 0.1% to about 10% by weight of mineral oil, wherein the progesterone is homogeneously dispersed in the elastomer.

In some embodiments, the present invention is directed to a monolithic intravaginal ring for treating a luteal phase defect in a patient in need thereof, the ring comprising about 10% to about 30%0/by weight of progesterone, about 60% to about 80% by weight of polysiloxane elastomer, and about 1% to about 8% by weight of a pharmaceutically acceptable hydrocarbon or glycerol esters of a fatty acid, wherein the progesterone is homogeneously dispersed in the elastomer.

In some embodiments, the present invention is directed to a monolithic intravaginal ring for treating a luteal phase defect in a patient in need thereof, the ring comprising about 10% to about 30% by weight of progesterone, about 60% to about 80% by weight of dimethylpolysiloxane elastomer, and about 1% to about 8% by weight of a mineral oil, wherein the progesterone is homogeneously dispersed in the elastomer.

In some embodiments, the present invention is directed to a monolithic intravaginal ring for treating a luteal phase defect in a patient in need thereof, the ring comprising about 20% to about 25% by weight of progesterone, about 65% to about 75% by weight of polysiloxane elastomer, and about 1% to about 6% by weight of a pharmaceutically acceptable hydrocarbon or glycerol esters of a fatty acid, wherein the progesterone is homogeneously dispersed in the elastomer.

In some embodiments, the present invention is directed to a monolithic intravaginal ring for treating a luteal phase defect in a patient in need thereof, the ring comprising about 20% to about 25% by weight of progesterone, about 65% to about 75% by weight of dimethylpolysiloxane elastomer, and about 1% to about 6% by weight of a mineral oil, wherein the progesterone is homogeneously dispersed in the elastomer, and wherein the progesterone is released from the monolithic intravaginal ring for about 18 days after administration to the patient.

The invention is directed to a process for making a monolithic intravaginal ring, the process comprising (a) mixing progesterone, a pharmaceutically acceptable hydrocarbon or glycerol esters of a fatty acid, and a polysiloxane to form a homogeneous mixture, (b) placing the homogeneous mixture into a mold and, (c) curing the homogeneous mixture in the mold to form a monolithic intravaginal ring comprising a polysiloxane elastomer, the progesterone, and the pharmaceutically acceptable hydrocarbon or glycerol esters of a fatty acid. In some embodiments of the present invention, the polysiloxane is vinyl end blocked.

In some embodiments, the mold is cured at about 60° C. to about 180° C., about 70° C. to about 150° C., about 80° C. to about 12° C., or about 85° C. to about 95° C. In some embodiments, the ring is cured outside the mold. In some embodiments, the process further comprises mixing a second polysiloxane into the homogeneous mixture prior to placing it into the mold. In some embodiments, the second polysiloxane is a cross-linker. In some embodiments, the cross-linker is dimethylmethylhydrogen polysiloxane. In some embodiments, the placing of the homogeneous mixture into the mold is by injection.

The present invention is directed to a method for treating a luteal phase defect in a patient in need thereof, the method comprising administering to a patient a monolithic intravaginal ring comprising (a) progesterone, (b) a dimethylpolysiloxane elastomer, and (c) a pharmaceutically acceptable hydrocarbon or glycerol esters of a fatty acid, wherein the ratio of progesterone to elastomer is about 1:1 to about 1:10, the progesterone is homogeneously dispersed in the elastomer, the ratio of progesterone to hydrocarbon or glycerol esters of a fatty acid is about 1:0.1 to about 1:100, and wherein the progesterone is released from the monolithic intravaginal ring for up to about 18 days after administration to the patient.

In some embodiments, the ratio of progesterone to elastomer is about 1:1 to about 1:10, about 1:1 to about 1:8, about 1:1 to about 1:6, about 1:1 to about 1:4, or about 1:2 to about 1:5.

In some embodiments, the ratio of progesterone to hydrocarbon or glycerol esters of a fatty acid is about 1:0.1 to about 1:100, about 1:0.1 to about 1:50, about 1:0.1 to about 1:25, about 1:0.1 to about 1:10, or about 1:0.1 to about 1:1.

The present invention is directed to a method for treating a luteal phase defect in a patient in need thereof, the method comprising administering to a patient a monolithic intravaginal ring comprising (a) progesterone, (b) a dimethylpolysiloxane elastomer, and (c) a pharmaceutically acceptable hydrocarbon or glycerol esters of a fatty acid, in a ratio of about 4:15:1, respectively (by weight), wherein the progesterone is homogeneously dispersed in the elastomer, and wherein the progesterone is released from the monolithic intravaginal ring for up to about 18 days after administration to the patient.

The present invention is directed to a method for treating a luteal phase defect in a patient in need thereof, the method comprising administering to a patient a monolithic intravaginal ring comprising (a) progesterone, (b) a dimethylpolysiloxane elastomer, and (c) a pharmaceutically acceptable hydrocarbon or glycerol esters of a fatty acid, in a ratio of about 20:90:1, respectively (by weight), wherein the progesterone is homogeneously dispersed in the elastomer, and wherein the progesterone is released from the monolithic intravaginal ring for up to about 18 days after administration to the patient.

The present invention is directed to a method for treating a luteal phase defect in a patient in need thereof, the method comprising administering to a patient a monolithic intravaginal ring comprising (a) progesterone, (b) a dimethylpolysiloxane elastomer, and (c) a pharmaceutically acceptable hydrocarbon or glycerol esters of a fatty acid, in a ratio of about 40:40:1, respectively (by weight), wherein the progesterone is homogeneously dispersed in the elastomer, and wherein the progesterone is released from the monolithic intravaginal ring for up to about 18 days after administration to the patient.

The present invention is directed to a method for treating a luteal phase defect in a patient in need thereof the method comprising administering to the patient a monolithic intravaginal ring comprising (a) about 10% to about 40% by weight of progesterone, (b) about 55% to about 90% by weight of a dimethylpolysiloxane elastomer, and (c) about 0.1% to about 10% by weight of a pharmaceutically acceptable hydrocarbon or glycerol esters of a fatty acid, wherein the progesterone is homogeneously dispersed in the elastomer, and wherein the progesterone is released from the monolithic intravaginal ring for up to about 18 days after administration to the patient.

The present invention is directed to a method for treating a luteal phase defect in a patient in need thereof, the method comprising administering to the patient a monolithic intravaginal ring comprising (a) about 15% to about 25% by weight of progesterone, (b) about 70% to about 80% by weight of a dimethylpolysiloxane elastomer, and (c) about 1% to about 10% by weight of a pharmaceutically acceptable hydrocarbon or glycerol esters of a fatty acid, wherein the progesterone is homogeneously dispersed in the elastomer, and wherein the progesterone is released from the monolithic intravaginal ring for up to about 18 days after administration to the patient.

In some embodiments, the intravaginal ring is replaced with a new ring after about 18 days following administration to the patient, after about 14 days following administration to the patient, after about 10 days following administration to the patient, after about 7 days following administration to the patient, after about 5 days following administration to the patient, after about 4 days following administration to the patient, after about 3 days following administration to the patient, or after about 2 days following administration to the patient. In accordance with the present invention, the intravaginal ring is not maintained longer than about 20 days before it is replaced with a new ring.

The intravaginal ring can be administered about one to seven days before embryo transfer, about two to six days before embryo transfer, about two to five days before embryo transfer, or about three to four days before embryo transfer. The administration of the intravaginal ring can be supplemented by other hormone administration, for example oral administration of estradiol.

In some embodiments, progesterone is administered via the intravaginal ring of the present invention for about 10 weeks, for about 8 weeks, for about 6 weeks, for about 4 weeks, for about 2 weeks, or for about 1 week.

In some embodiments, the present invention is directed to a method for treating a luteal phase defect in a patient in need thereof, the method comprising administering to the patient a monolithic intravaginal ring comprising (a) progesterone, (b) MED-4840, and (c) a pharmaceutically acceptable hydrocarbon or glycerol esters of a fatty acid, wherein the ratio of progesterone to MED-4840 is about 1:1 to about 1:10, the progesterone is homogeneously dispersed in the elastomer, the ratio of progesterone to hydrocarbon or glycerol esters of a fatty acid is about 1:0.1 to about 1:100, wherein the progesterone is released from the intravaginal ring at about 15 mg/day to about 25 mg/day in vivo, and wherein the intravaginal ring is replaced after about every 7 days following administration to the patient.

In some embodiments, the present invention is directed to a method for treating a luteal phase defect in a patient in need thereof, the method comprising administering to the patient a monolithic intravaginal ring comprising (a) progesterone, (b) a dimethylpolysiloxane elastomer, and (c) mineral oil, in a ratio of about 4:15:1, respectively, wherein the progesterone is homogeneously dispersed in the elastomer, and released from the intravaginal ring at about 15 mg/day to about 25 mg/day in vivo, and wherein the intravaginal ring is replaced after about every 7 days following administration to the patient.

In some embodiments, the present invention is directed to a method for treating a luteal phase defect in a patient in need thereof, the method comprising administering to a patient a monolithic intravaginal ring comprising (a) about 20% progesterone, (b) about 75% MED-4840, and (c) about 5% mineral oil, wherein the progesterone is homogeneously dispersed in the elastomer, wherein the progesterone is released from the intravaginal ring at about 15 mg/day to about 25 mg/day in vivo, and wherein the intravaginal ring is replaced after about every 7 days following administration to the patient.

The following examples are for the purpose of illustration of the invention only and are not intended in any way to limit the scope of the present invention. It will thus be readily apparent to one skilled in the art that varying substitutions and modifications may be made to the invention disclosed herein without departing from the scope and spirit of the invention.

EXAMPLES

Example 1

Figure 2:
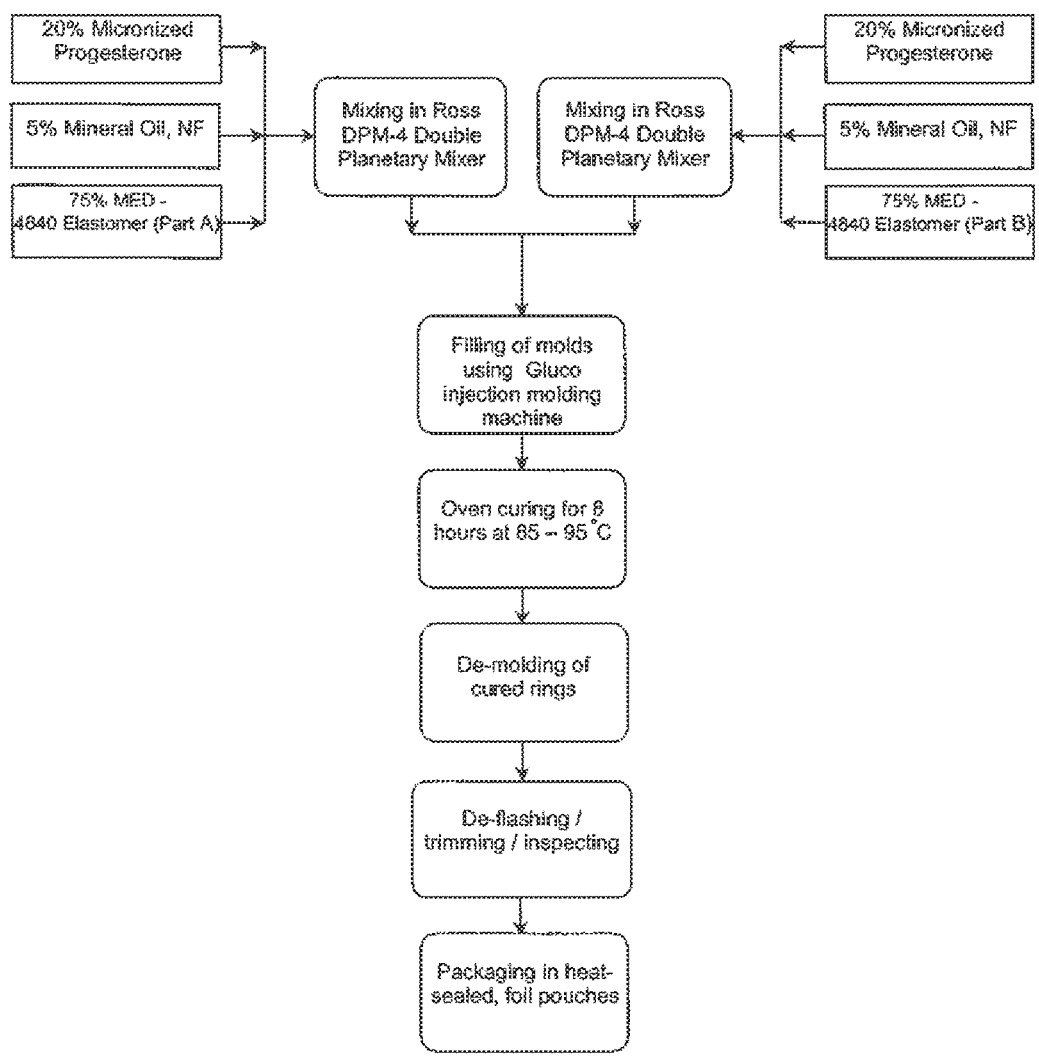
FIG. 2 depicts a process flow chart representing a process for preparing monolithic intravaginal rings of the present invention.

FIG. 2 depicts a process flow chart representing a process for preparing a monolithic intravaginal ring of the present invention. Micronized progesterone, MED-4840 elastomer part A, and mineral oil were combined to form a homogeneous mixture ("the part A mix"). Micronized progesterone, MED-4840 elastomer part B, and mineral oil were combined to form a second homogeneous mixture ("the part B mix").

The part A mix was prepared by placing about 20% (by weight of the final product) micronized progesterone, about 75% (by weight of the final product) MED-4840 part A polysiloxane, and about 5% (by weight of the final product) mineral oil in a Ross DPM-4 mixer (Ross double planetary mixer and dispenser supplied by Charles Ross & Son, Hauppauge, N.Y.), where the ingredients were mixed and degassed under vacuum for about 30 minutes. The part A mix was then transferred to pre-weighed disposable cartridges.

The part B mix was prepared by placing about 20% (by weight of the final product) micronized progesterone, about 75% (by weight of the final product) MED-4840 part B polysiloxane and about 5% (by weight of the final product) mineral oil in a Ross DPM-4 mixer, where the ingredients were mixed and degassed under vacuum for about 30 minutes. The part B mix was then transferred to pre-weighed disposable cartridges.

The part A mix and the part B mix cartridges were then placed on separate pumps of a Gluco P20LS injection molding machine (supplied by Gluco, Jenison, Mich.). The machine then injected both the A and B mixes at a 1:1 ratio into a static mixer to produce a homogeneous mix in-line. The in-line homogeneous mix was immediately injected into a multi-cavity mold for filling at ambient temperature.

The filled molds were removed from the machine and transferred to a Grieve oven (Grieve Corp., Round Lake, Ill.) for curing at about 90° C. for about eight hours. The molds were then allowed to cool to room temperature and disassembled to remove the rings. Entry and exit runners and flashing were removed from the rings, which were then trimmed prior to packaging in heat-sealed foil pouches.

The process yielded a monolithic intravaginal ring with a composition as listed in Table 1, with an outside diameter of about 55 mm, an inside diameter of about 38 mm, and a cross-sectional diameter of about 8.5 mm (as depicted in FIG. 1).

Figure 5:
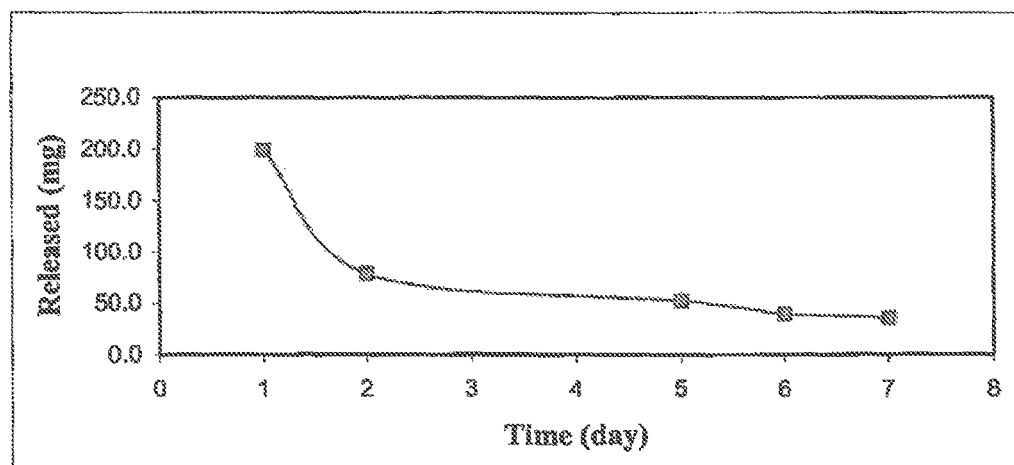
FIG. 5 shows the in vitro dissolution data and profile of a progesterone intravaginal ring of the present invention.

The in vitro dissolution profile of the intravaginal ring was determined using an Orbital shaker containing 250 mL of 0.008 M SDS at 37° C. at 50 rpm. These results are listed in FIG. 5. When administered to the vaginal tract of a patient, the intravaginal ring releases about 10 mg/day to about 30 mg/day of progesterone over about 7 days.

TABLE 1

Composition of the monolithic intravaginal ring of Example 1

|  | (mass/g) | (% wt of ring) |
| --- | --- | --- |
| Micronized Progesterone | 1.8 | 20 |
| Mineral Oil | 0.45 | 5 |
| MED-4840 Part A | 3.375 | 37.5 |
| MED-4840 Part B | 3.375 | 37.5 |
| Total | 9.000 | 100 |

Example 2

A pharmacodynamic study to compare an intravaginal ring of Example 1 to a progesterone vaginal gel for luteal phase replacement was conducted.

This was a single-center, open-label, randomized, active-controlled, comparative, pharmacodynamic study to evaluate a single dose of progesterone, delivered by vaginal ring, for resultant endometrial transformation and luteal phase replacement. The study had 2 treatment arms. One investigator enrolled and randomized 20 eligible women aged 18-50, with 10 women per treatment arm (21 subjects were randomized and one subject discontinued from the vaginal gel treatment arm when she was found to have cervical dysplasia on her Pap smear). The overall study duration for each patient was approximately 1½ months. The subject demographics are shown in Table 2.

TABLE 2

Subject Demographics

| | Mock Cycle | | ET Cycle | |
|---|---|---|---|---|
| | Progesterone Vaginal Ring N = 10 | Progesterone Vaginal Gel N = 11 | Progesterone Vaginal Ring N = 5 | Progesterone Vaginal Gel N = 4 |
| Race: | | | | |
| African-American | 2 (20.0%) | 3 (27.3%) | 1 (20.0%) | 0 (0.0%) |
| Caucasian | 8 (80.0%) | 8 (72.7%) | 4 (80.0%) | 4 (100%) |
| Age (yrs): | | | | |
| Mean (SD) | 41.0 (5.42) | 39.1 (6.12) | 43.0 (3.39) | 39.8 (7.23) |
| Min/Max | 30.0/47.0 | 30.0/49.0 | 38.0/47.0 | 33.0/50.0 |
| Body Mass Index (kg/m$^2$): | | | | |
| Mean (SD) | 27.7 (4.84) | 27.5 (6.73) | 25.4 (2.0) | 25.2 (3.63) |
| Min/Max | 21.7/36.9 | 19.6/40.5 | 23.2/27.5 | 20.2/28.4 |

All patients met all inclusion and none of the exclusion criteria as specified in the protocol. Continued participation in the study depended on the patient meeting the protocol requirement at the randomization visit. The study duration was 31 days plus two weeks of post-treatment follow-up. In the first 14 days, estradiol pre-treatment was given in attempt to generate a proliferative phase of the endometrium.

Subjects enrolled in the mock cycle received oral contraceptive pills ("OCPs") for 2 weeks and a GnRH agonist (Lupron®, TAP Pharmaceuticals, Chicago, Ill.) to suppress ovarian function. The GnRH agonist was initiated on day 8 of the OCPs in the cycle preceding the mock and/or transfer cycle and continued until estradiol patches were initiated. The estradiol regimen was determined by the site's mock cycle protocol and/or the clinical investigator's discretion. Estradiol pre-treatment was generally administered in a step-up fashion (0.2 mg days 1-7, 0.3 mg days 8-11 and 0.4 mg days 12-14 every other day, Vivelle patches) to generate a proliferative phase of the endometrium.

Subjects with an endometrial thickness >6 mm were randomized in a 1:1 fashion to either a progesterone intravaginal ring (10-30 mg/day, Duramed Research, Inc., Bala Cynwyd, Pa.) or a progesterone vaginal gel (Crinone®, 180 mg/day, Columbia Laboratories, Inc., Livingston, N.J.) and taught to administer the product. A progesterone intravaginal ring 10-30 mg/day (in vitro release rate) or progesterone vaginal gel (180 mg/day), together with estradiol (per the site's protocol, e.g., 0.2 mg/day), was administered over the next 18 days to transform the endometrium to the secretory phase. The progesterone intravaginal ring was replaced one time on day 8, while the vaginal gel was administered twice a day for the full 18 days of progesterone dosing. Serum progesterone and estradiol samples were collected at cycle day 0, 14, 15, 16, 18, 21, 22, 23, 25, 28, and 31. An endometrial biopsy was performed on cycle day 25 or 26 and endometrial dating was performed according to Noyes et al., Fertil. Steril., 1:3-25 (1950). Intravaginal ring compliance was determined at each study visit. Vaginal colposcopy was performed at screening and on cycle day 31 to determine whether there was potential vaginal and cervical irritation.

The objectives of the study were to determine in women with clinical or medically-induced agonadism (who were administered the intravaginal ring) (a) the proportion of patients with adequate endometrial transformation (on endometrial biopsy) as determined by histological dating of the endometrium, (b) progesterone and estradiol levels in the serum obtained from patients, and (c) the safety and tolerability of progesterone delivered by an intravaginal ring as compared with a progesterone vaginal gel. The study was performed on twenty patients with an estrogen-primed endometrium.

Subjects were women aged 18-50 with clinical or medically-induced agonadism who were eligible for oocyte donation. Subjects with a history of more than two failed donor egg cycles, significant prior uterine surgery, hysterectomy, or clinically significant uterine pathology were excluded from the study.

The intravaginal ring of Example 1 was administered to the subject, and the duration of the dosing regimen lasted 18 days, wherein the intravaginal ring was replaced once in the 18 day period, on day 8. In subjects that were administered the progesterone vaginal gel, the vaginal application of 180 mg/day for 18 days was dosed at 90 mg twice a day.

The primary efficacy measure was the presence or absence of adequate secretory transformation of the endometrium as determined by biopsy on either cycle day 25 or 26. The proportion of patients having an in-phase biopsy and adequate endometrial secretory transformation determined by histological dating of the endometrium, as defined by the histological test results, was calculated. The intravaginal ring of Example 1 adequately transformed the endometrium to secretory phase in 8 out of 10 patients while the vaginal gel 180 mg/day did so in 10 out of 10 patients.

However, additional outside factors may have contributed to the failure in the two patients who did not exhibit endometrial transformation. One subject had a non-datable endometrium; predominantly inactive with tubal metaplasia, but showing small foci of secretory exhaustion, suggestive of an uneven end-organ response to the hormonal milieu (i.e., irregular ripening). There was a fibroid found in surgery post-study, which could have affected blood supply to the endometrium. Post-surgery, the subject went through a mock cycle with micronized progesterone 200 mg t.i.d. and underwent a biopsy that showed adequate transformation. This same subject underwent a donor egg IVF using micronized progesterone that resulted in a negative βhCG. The subject is considering one more IVF attempt with a donor egg. The second subject was a 37 year-old with gonadal dysgenesis (streak ovaries and ovarian failure) and no periods since birth who exhibited a mixed inactive and exhausted secretory endometrium; features favored late secretory phase, but no precise dating was possible. This subject was screened twice for the study, and after the first estradiol pre-treatment had an endometrial lining <6 mm. The subject was allowed to re-screen for the study; and after the second screening and estradiol pre-treatment, the subject had an endometrial lining >6 mm. Post-study, the subject went through a mock cycle with IM progesterone, and underwent a biopsy that showed adequate transformation. This same subject underwent a donor egg IVF using IM progesterone (50 mg) that resulted in a positive (hCG and an ongoing pregnancy with delivery.

Figure 3:
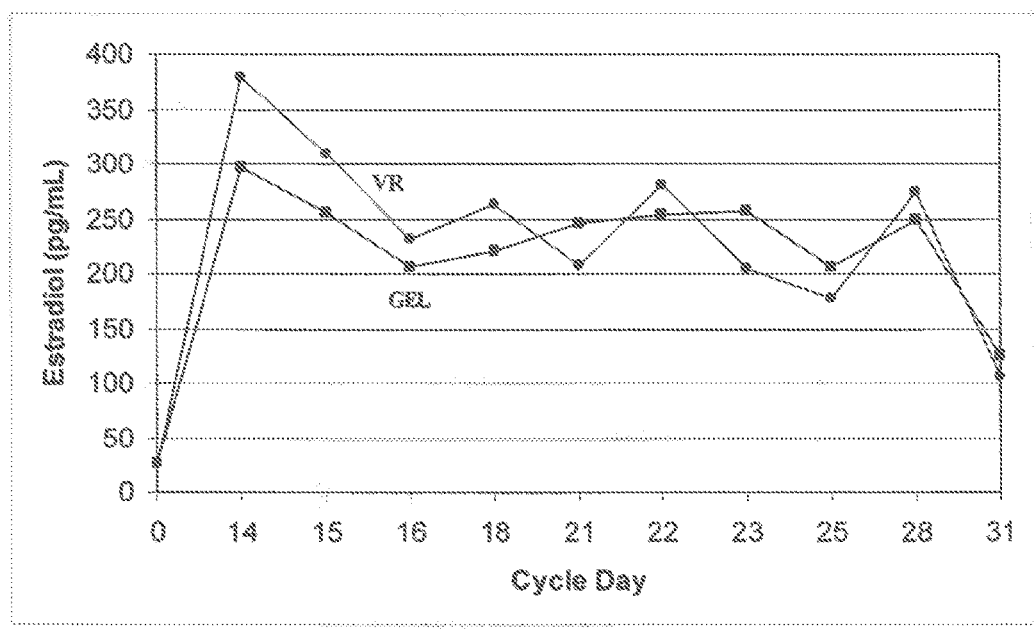
FIG. 3 shows a comparison of the mean serum estradiol levels in a patient following administration of a progesterone intravaginal ring of the present invention or a progesterone vaginal gel.
Figure 4:
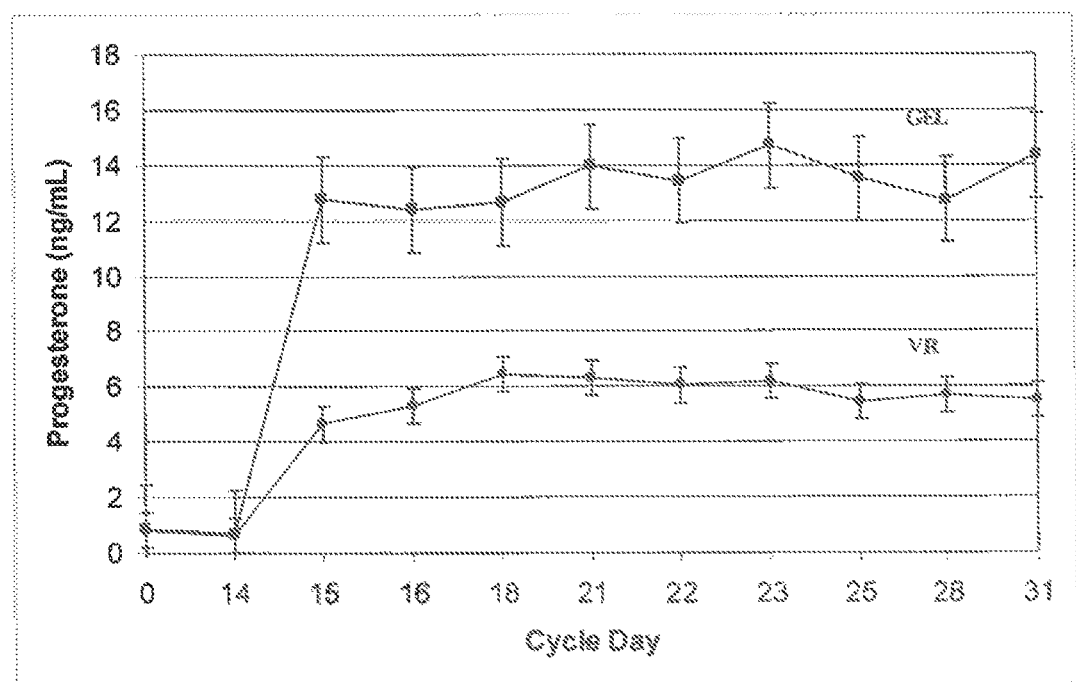
FIG. 4 shows a comparison of the mean serum progesterone levels in a patient following administration of a progesterone intravaginal ring of the present invention or a progesterone vaginal gel.

Estradiol serum levels in the intravaginal ring treatment group were comparable with that of the Crinone® group, while progesterone serum levels in the intravaginal ring treatment group were on average lower than those for Crinone® (6.02 ng/mL vs. 14.18 ng/mL). Estradiol serum levels of the treatment groups at various time points is shown below in Table 3 and schematically in FIG. 3. Progesterone serum levels of the treatment groups at various time points is shown below in Table 4 and schematically in FIG. 4.

TABLE 3

Estradiol Serum Levels and Changes During the Study

| Estradiol (ng/mL) | - Progesterone Vaginal Ring - | | | | - 8% Progesterone Vaginal Gel - | | | | - Total - | | | |
|---|---|---|---|---|---|---|---|---|---|---|---|---|
| | N | Mean (Std) | Median | (Min, Max) | N | Mean (Std) | Median | (Min, Max) | N | Mean (Std) | Median | (Min, Max) |
| Beginning | 10 | 19.8 (16.29) | 10.0 | (10.0, 61.0) | 10 | 32.4 (44.61) | 10.0 | (10.0, 152.0) | 20 | 26.1 (33.32) | 10.0 | (10.0, 152.0) |
| Cycle Day 14 | 10 | 280.4 (91.69) | 264.0 | (172.0, 410.0) | 10 | 345.1 (100.85) | 339.0 | (232.0, 498.0) | 20 | 312.8 (99.50) | 304.0 | (172.0, 498.0) |
| Change from Beginning to Day 14 | 10 | 260.6 (86.82) | 242.5 | (162.0, 394.0) | 10 | 312.7 (121.15) | 318.5 | (110.0, 488.0) | 20 | 286.7 (106.01) | 277.5 | (110.0, 488.0) |
| Cycle Day 15 | 10 | 229.0 (145.69) | 205.0 | (108.0, 616.0) | 10 | 283.0 (111.48) | 274.5 | (141.0, 453.0) | 20 | 256.0 (129.26) | 208.5 | (108.0, 616.0) |
| Change from Beginning to Day 15 | 10 | 209.2 (148.51) | 180.0 | (98.0, 606.0) | 10 | 250.6 (118.12) | 201.5 | (112.0, 443.0) | 20 | 229.9 (132.31) | 181.5 | (98.0, 606.0) |
| Cycle Day 16 | 10 | 188.2 (93.35) | 160.5 | (61.6, 346.0) | 10 | 229.9 (102.28) | 207.5 | (65.9, 408.0) | 20 | 209.0 (97.68) | 192.0 | (61.6, 408.0) |
| Change from Beginning to Day 16 | 10 | 168.4 (87.00) | 150.5 | (50.0, 293.0) | 10 | 197.5 (112.30) | 188.0 | (25.0, 398.0) | 20 | 182.9 (98.91) | 169.0 | (25.0, 398.0) |
| Cycle Day 18 | 10 | 198.2 (74.44) | 199.5 | (84.1, 322.0) | 10 | 232.9 (145.87) | 186.5 | (102.0, 501.0) | 20 | 215.6 (114.11) | 198.0 | (84.1, 501.0) |
| Change from Beginning to Day 18 | 10 | 178.4 (71.55) | 172.0 | (61.1, 296.0) | 10 | 200.5 (159.59) | 176.5 | (−50.0, 491.0) | 20 | 189.5 (120.90) | 172.0 | (−50.0, 491.0) |
| Cycle Day 21 | 10 | 216.5 (139.59) | 167.5 | (64.8, 496.0) | 10 | 186.6 (82.09) | 172.5 | (66.0, 351.0) | 20 | 201.5 (112.50) | 167.5 | (64.8, 496.0) |
| Change from Beginning to Day 21 | 10 | 196.7 (142.31) | 143.0 | (41.8, 486.0) | 10 | 154.2 (96.53) | 152.5 | (13.0, 341.0) | 20 | 175.4 (120.34) | 152.5 | (13.0, 486.0) |
| Cycle Day 22 | 10 | 221.0 (126.25) | 184.0 | (76.5, 504.0) | 10 | 259.1 (86.13) | 226.0 | (187.0, 436.0) | 20 | 240.0 (106.99) | 201.5 | (76.5, 504.0) |
| Change from Beginning to Day 22 | 10 | 201.2 (119.09) | 174.0 | (53.5, 478.0) | 10 | 226.7 (95.57) | 201.0 | (74.0, 380.0) | 20 | 213.9 (105.90) | 183.0 | (53.5, 478.0) |
| Cycle Day 23 | 10 | 236.8 (146.75) | 157.5 | (92.0, 514.0) | 10 | 212.7 (79.13) | 191.5 | (135.0, 382.0) | 20 | 224.8 (115.41) | 172.5 | (92.0, 514.0) |
| Change from Beginning to Day 23 | 10 | 217.0 (144.87) | 141.0 | (64.0, 504.0) | 10 | 180.3 (75.48) | 156.5 | (106.0, 372.0) | 20 | 198.7 (113.99) | 151.5 | (64.0, 504.0) |
| Cycle Day 25 | 10 | 190.5 (81.33) | 169.0 | (100.0, 355.0) | 10 | 193.1 (145.48) | 142.5 | (63.8, 539.0) | 20 | 191.8 (114.72) | 154.5 | (63.8, 539.0) |
| Change from Beginning to Day 25 | 10 | 170.7 (77.35) | 156.5 | (90.0, 329.0) | 10 | 160.7 (123.48) | 123.0 | (53.8, 483.0) | 20 | 165.7 (100.41) | 135.0 | (53.8, 483.0) |
| Cycle Day 28 | 10 | 223.7 (104.99) | 184.0 | (102.0, 418.0) | 10 | 282.1 (158.28) | 309.0 | (88.9, 610.0) | 20 | 252.9 (134.11) | 212.0 | (88.9, 610.0) |
| Change from Beginning to Day 28 | 10 | 203.9 (98.75) | 174.0 | (79.0, 392.0) | 10 | 249.7 (153.35) | 247.0 | (78.9, 600.0) | 20 | 226.8 (127.72) | 192.5 | (78.9, 600.0) |
| Cycle Day 31 | 10 | 124.2 (73.10) | 123.0 | (34.0, 296.0) | 10 | 115.3 (63.02) | 96.0 | (47.0, 234.0) | 20 | 119.7 (66.58) | 112.5 | (34.0, 296.0) |
| Change from Beginning to Day 31 | 10 | 104.4 (69.67) | 96.0 | (24.0, 270.0) | 10 | 82.9 (54.81) | 71.5 | (17.0, 178.0) | 20 | 93.6 (62.00) | 79.5 | (17.0, 270.0) |

TABLE 4

| Progesterone | - Progesterone Vaginal Ring - | | | | - 8% Progesterone Vaginal Gel - | | | | - Total - | | | |
|---|---|---|---|---|---|---|---|---|---|---|---|---|
| (ng/mL) | N | Mean(Std) | Median | (Min, Max) | N | Mean(Std) | Median | (Min, Max) | N | Mean(Std) | Median | (Min, Max) |
| Begininng | 10 | 0.9 (0.71) | 0.6 | (0.2, 2.5) | 10 | 0.9 (0.32) | 0.9 | (0.6, 1.6) | 20 | 0.9 (0.53) | 0.8 | (0.2, 2.5) |
| Cycle Day 14 | 10 | 0.7 (0.33) | 0.7 | (0.1, 1.4) | 10 | 0.8 (0.24) | 0.8 | (0.5, 1.2) | 20 | 0.7 (0.28) | 0.7 | (0.1, 1.4) |
| Change from Beginning to Day 14 | 10 | −0.2 (0.54) | −0.1 | (−1.5, 0.5) | 10 | −0.1 (0.21) | −0.2 | (−0.6, 0.2) | 20 | −0.2 (0.40) | −0.1 | (−1.5, 0.5) |
| Cycle Day 15 | 10 | 5.2 (2.00) | 4.7 | (3.3, 9.0) | 10 | 11.9 (6.48) | 11.6 | (3.6, 26.0) | 20 | 8.5 (5.79) | 6.6 | (3.3, 26.0) |
| Change from Beginning to Day 15 | 10 | 4.3 (1.77) | 3.4 | (2.7, 7.3) | 10 | 10.9 (6.46) | 10.5 | (2.6, 25.2) | 20 | 7.6 (5.75) | 5.8 | (2.6, 25.2) |
| Cycle Day 16 | 10 | 5.6 (1.85) | 5.6 | (3.5, 9.2) | 10 | 13.3 (3.95) | 14.0 | (5.8, 19.7) | 20 | 9.4 (4.96) | 8.5 | (3.5, 19.7) |
| Change from Beginning to Day 16 | 10 | 4.7 (1.73) | 4.5 | (3.0, 8.5) | 10 | 12.4 (3.89) | 12.6 | (5.2, 18.9) | 20 | 8.5 (4.92) | 7.3 | (3.0, 18.9) |
| Cycle Day 18 | 10 | 6.7 (1.96) | 7.1 | (4.0, 9.5) | 10 | 13.0 (4.76) | 12.8 | (6.9, 23.4) | 20 | 9.8 (4.80) | 8.7 | (4.0, 23.4) |
| Change from Beginning to Day 18 | 10 | 5.8 (1.90) | 5.7 | (3.4, 8.9) | 10 | 32.0 (4.79) | 11.9 | (6.3, 22.6) | 20 | 8.9 (4.80) | 7.7 | (3.4, 22.6) |
| Cycle Day 21 | 10 | 6.6 (1.70) | 5.9 | (4.6, 9.4) | 10 | 13.2 (4.81) | 12.2 | (7.4, 22.4) | 20 | 9.9 (4.89) | 8.7 | (4.6, 22.4) |
| Change from Beginning to Day 21 | 10 | 5.7 (1.80) | 5.2 | (3.2, 8.8) | 10 | 12.3 (4.77) | 11.3 | (6.8, 21.6) | 20 | 9.0 (4.89) | 7.7 | (3.2, 21.6) |
| Cycle Day 22 | 10 | 6.5 (2.00) | 6.2 | (3.9, 9.7) | 10 | 14.8 (6.02) | 15.8 | (6.6, 26.3) | 20 | 10.6 (6.11) | 8.7 | (3.9, 26.3) |
| Change from Beginning to Day 22 | 10 | 5.5 (2.01) | 5.0 | (3.4, 8.5) | 10 | 13.9 (6.00) | 14.5 | (6.0, 25.5) | 20 | 9.7 (6.10) | 7.9 | (3.4, 25.5) |
| Cycle Day 23 | 10 | 6.5 (1.80) | 6.5 | (3.5, 9.3) | 10 | 16.9 (10.31) | 14.5 | (7.2, 38.5) | 20 | 11.7 (8.98) | 7.9 | (3.5, 38.5) |
| Change from Beginning to Day 23 | 10 | 5.6 (1.92) | 5.3 | (3.0, 8.7) | 10 | 16.0 (10.33) | 13.5 | (5.9, 37.7) | 20 | 10.8 (9.00) | 7.2 | (3.0, 37.7) |
| Cycle Day 25 | 10 | 5.7 (1.54) | 5.8 | (3.7, 7.8) | 10 | 14.7 (6.37) | 16.2 | (5.4, 26.8) | 20 | 10.2 (6.46) | 7.1 | (3.7, 26.8) |
| Change from Beginning to Day 25 | 10 | 4.8 (1.48) | 4.7 | (3.1, 7.4) | 10 | 13.8 (6.42) | 15.2 | (4.8, 26.0) | 20 | 9.3 (6.47) | 6.1 | (3.1, 26.0) |
| Cycle Day 28 | 10 | 5.7 (1.38) | 6.0 | (3.8, 8.0) | 10 | 15.1 (7.19) | 15.7 | (6.2, 29.0) | 20 | 10.4 (6.96) | 6.9 | (3.8, 29.0) |
| Change from Beginning to Day 28 | 10 | 4.8 (1.46) | 4.7 | (3.2, 7.8) | 10 | 14.2 (7.07) | 15.0 | (5.5, 27.7) | 20 | 9.5 (6.91) | 5.9 | (3.2, 27.7) |
| Cycle Day 31 | 10 | 5.7 (1.52) | 5.5 | (3.2, 8.1) | 10 | 14.7 (6.54) | 14.4 | (3.7, 27.3) | 20 | 10.2 (6.51) | 7.7 | (3.2, 27.3) |
| Change from Beginning to Day 31 | 10 | 4.8 (1.52) | 4.7 | (2.6, 7.7) | 10 | 13.7 (6.57) | 13.8 | (3.1, 26.5) | 20 | 9.3 (6.52) | 6.6 | (2.6, 26.5) |

Also in this study the intravaginal ring was observed to be as safe as the vaginal gel, except for the observation that most patients in the intravaginal ring treatment group had mild vaginal bleeding/spotting near the end of the treatment. A summary of breakthrough bleeding/spotting for the treatment groups and in individual subjects is shown in Tables 5 and 6, respectively.

TABLE 5

Vaginal Bleeding/Spotting During Study for the Treatment Groups

| Visit | 8% Progesterone Vaginal Ring (N = 10) | Progesterone Vaginal Gel (N = 11) | Total (N = 21) |
|---|---|---|---|
| Total Bleeding/Spotting Patients | 9 (90.00) | 5 (45.45) | 14 (66.67) |
| Cycle Day 25 | 5 (50.00) | 4 (36.36) | 9 (42.86) |
| Cycle Day 26 | 4 (40.00) | 3 (27.27) | 7 (33.33) |
| Cycle Day 27 | 4 (40.00) | 1 (9.09) | 5 (23.81) |
| Cycle Day 28 | 6 (60.00) | 0 (0.00) | 6 (28.57) |
| Cycle Day 29 | 8 (80.00) | 0 (0.00) | 8 (38.10) |
| Cycle Day 30 | 9 (90.00) | 0 (0.00) | 9 (42.86) |
| Cycle Day 31 | 7 (70.00) | 0 (0.00) | 7 (33.33) |

TABLE 6

Summary of Breakthrough Vaginal Bleeding/Spotting in Individual Subjects

| Patient # | Study Drug | Vaginal bleeding before biopsy? | Phase | Cycle Day by Histologic Dating | Vaginal bleeding after biopsy, but before Visit 9 (Cycle Day 28)? | Vaginal bleeding on/after Visit 9 (Cycle Day 28)? | AEs reported |
|---|---|---|---|---|---|---|---|
| 0103 | VR | | Secretory | 23 | | | Metrorrhagia, Onychomycosis |
| 0105 | VR | | Inactive | N/A | | | Metrorrhagia, Myalgia |
| 0107 | VR | | Secretory | 23 | light spotting | light spotting | Metrorrhagia, Limb Discomfort |
| 0109 | VR | | Secretory | 24 | light spotting | light spotting | Metrorrhagia, Dysmenorrhoea |
| 0113 | VR | | Secretory | 23 | | | Metrorrhagia |
| 0114 | VR | | Secretory | 25 | light spotting | | Metrorrhagia, Nasopharyngitis |
| 0123 | VR | Cycle Day 21, Scant amount of pink tinged mucous on VR | Mixed Pattern | N/A | | | Vaginal Discharge Upper Respiratory Tract Infection (URTI), Skin Irritation |
| 0124 | VR | | Secretory | 25** | light spotting | | Metrorrhagia |
| 0127 | VR | | Secretory | 23 | red/brown spotting | | Metrorrhagia, Nausea |
| 0129 | VR | | Secretory | 25 | Spotting | | Metrorrhagia, URTI, Ear Pain Breast Discomfort, Post Precedural Complication |
| 0102 | Gel | | Secretory | 25 | moderate to heavy | | N/A |
| 0106 | Gel | | Secretory | 23 | light spotting | | Pelvic Pain, Sinus Headaches, Pharyngolaryngeal Pain |
| 0108 | Gel | | Secretory | 23 | | | Nausea |
| 0111 | Gel | Prior to Visit 1, moderate to heavy | Secrctoty | 24 | light spotting | | Headaches, URTI |
| 0115 | Gel | | Secretory | 25 | | | URTI, Uterine Cervical Erosion, Vaginal Erosion |

TABLE 6-continued

Summary of Breakthrough Vaginal Bleeding/Spotting in Individual Subjects

| Patient # | Study Drug | Vaginal bleeding before biopsy? | Phase | Cycle Day by Histologic Dating | Vaginal bleeding after biopsy, but before Visit 9 (Cycle Day 28)? | Vaginal bleeding on/after Visit 9 (Cycle Day 28)? | AEs reported |
|---|---|---|---|---|---|---|---|
| 0122 | Gel | Prior to Visit 0 - during estradiol pre-treatment (moderate) | Secretory | 24 | light spotting | | Metrorrhagia, Headache, Withdrawl Bleed, Dysmenorrhoea |
| 0125 | Gel | | Secretory | 25 | | | Vulvovaginal Discomfort Abdominal Pain, Post Procedural Complication |
| 0126 | Gel | | Secretory | 25 | one spec dry blood | | Breast Discomfort, Cervical Polyp, Abdominal Pain |
| 0128 | Gel | | Secretory | 24 | light spotting | | Abdominal Pain, Post Procedural Complication |
| 0130 | Gel | | Secretory | 24 | | | Abdominal Pain Lower |

*vaginal bleeding after biopsy cases were reported by the site via email or phone; vaginal bleeding after biopsy was not considered an AE, as it is an expected result of the procedure; therefore, the above information was not captured on the CRFs, nor entered into the database
**patchy decidualization of stroma giving a range of appearances from POD 8 to POD 11

Subjects with adequate secretory endometrial transformation in the mock cycle who had accepted an oocyte donor and were synchronized with this donor were invited to participate in a follow-on embryo transfer cycle. Subjects were kept on the same progesterone treatment to which they had been randomized in the mock cycle. For subjects in the intravaginal ring group, a new intravaginal ring was placed at the time of transfer, and the intravaginal ring was scheduled to be replaced weekly until the pregnancy test was performed 2 weeks after embryo transfer. Subjects in the vaginal gel group continued to self-administer the vaginal gel twice daily until 2 weeks after embryo transfer. If a pregnancy was detected, the estradiol replacement was continued for a total of 8 weeks and the progesterone for a total of 10 weeks after embryo transfer. Pelvic ultrasound was performed at 8 weeks and 12 weeks to confirm a clinical pregnancy. Follow-up of any pregnancies continued until delivery.

Biochemical pregnancy, clinical pregnancy (8 and 12 weeks of pregnancy), and live birth rates were assessed. A biochemical pregnancy was defined as a transient increase in βhCG levels, followed by a decrease. A clinical pregnancy was defined by the visualization of a gestational sac with fetal heart motion on ultrasound. The primary efficacy measure in the embryo transfer cycle was the clinical pregnancy rate at 8 weeks of pregnancy, where the gestational age (duration of pregnancy) in weeks was defined as commencing 2 weeks prior to embryo transfer, which would correlate in a normally ovulating and cycling woman with the first day of her last menstrual period. Secondary outcome measures in the embryo transfer cycle included clinical pregnancy rates at 12 weeks of pregnancy and live birth rates.

A total of 11 subjects consented, with 9 subjects undergoing an embryo transfer. There were a total of 5 transfers in the intravaginal ring treatment group and 4 in the vaginal gel treatment group. Of these transfers, 4 of 5 (80%) intravaginal ring subjects and 1 of 4 (25%) vaginal gel subjects became pregnant (confirmed 2 weeks after embryo transfer) resulting in 4 term singleton deliveries and one set of twins delivering at 34 weeks. The full results of the pregnancies and live births are outlined in Table 7. Individual subject data is shown in Table 8. There were no biochemical pregnancies and no miscarriages in the pregnant subjects. One of the pregnant intravaginal ring subjects was discontinued from the study and switched to intramuscular progesterone due to the bleeding pattern at 9 weeks of pregnancy (7 weeks after embryo transfer).

TABLE 7

Biochemical Pregnancy, Clinical Pregnancy, and Live Birth Rates

| | Progesterone Vaginal Ring | Progesterone Vaginal gel | All subjects |
|---|---|---|---|
| Number of fresh transfers | 5 | 4 | 9 |
| Number of embryos transferred | 2 | 2 | 2 |
| Biochemical pregnancy [N (%)] | 0 (0) | 0 (0) | 0 (0) |
| Miscarriages [N (%)] | 0 (0) | 0 (0) | 0 (0) |
| 8 week clinical pregnancy [N (%)] | 4 (80) | 1 (25) | 5 (56) |
| 12 week clinical pregnancy [N (%)] | 3* (60) | 1 (25) | 4* (44) |
| Livebirth [N (%)] | 3* (60) | 1 (25) | 4* (44) |

*One subject who became pregnant on the progesterone VR was discontinued from the study at Week 9 of pregnancy due to vaginal bleeding. This subject was switched to IM progesterone and sustained the pregnancy until a live birth.

TABLE 8

Individual Subject Data

| Patient No. | Study Drug | Pregnancy? | Cramping During Study? | Vaginal spotting during study? | Vaginal bleeding during study? | AEs reported |
|---|---|---|---|---|---|---|
| 0103 | VR | Yes [switched to IM progesterone due to vaginal bleeding; withdrawn from study; live birth] | ET + 24 days<br>ET + 43 days<br>ET + 44 days | ET + 24 days<br>ET + 25 days<br>ET + 26 days | ET + 46 days | Nausea-interminent; vomiting-intermittent; pelvic cramping; vaginal spotting; vaginal bleeding; lower quadrant abdominal cramping |
| 0107 | VR | No | | | | Light-headed; sore throat |
| 0109 | VR | Yes (twins) [Completed study] | | ET + 9 days<br>ET + 20 days<br>ET + 21 days<br>ET + 23-28 days<br>ET + 30-41 days<br>ET + 43-49 days | ET + 28 days<br>ET + 29 days | Vulvovaginal candidiasis; vaginal spotting (reports progressively increased spotting toward time of vaginal ring change; cessation of spotting when new ring is inserted); gestational diabetes; mild hypertension; indigestion-intermittent |
| 0113 | VR | Yes (twins) [Completed study; no reported spotting/bleeding] | | | | Nausea-intermittent; indigestion-intermittent; diarrhea-intermittent |
| 0114 | VR | Yes | ET + 34 days | ET + 34 days<br>ET + 38 days<br>ET + 40-47 days | | Vaginal Spotting; headache-intermittent; insomnia; pelvic cramps-intermittent; upper respiratory infection |
| 0102 | Gel | No | | | | Upper respiratory infection |
| 0106 | Gel | No - discontinued prior to embryo transfer | | | | Sore throat |
| 0115 | Gel | No | ET + 2-9 days | | | Indigestion; cold sore-oral; pelvic cramping; pelvic pressure; seasonal allergies; headache |
| 0122 | Gel | No | ET + 5-11 days | | | Headache, intermittent; lower abdominal cramping, intermittent; upper respiratory infection |
| 0125 | Gel | Yes [Completed study] | | ET + 41 days | | Intermittent nausea; left arm axilla, swollen glands; left axilla tenderness; left axilla, swollen glands; lower abdominal cramping; upper respiratory infection; vaginal spotting |

The treatment emergent adverse events reported were similar among the two treatment groups, with a few exceptions. More adverse vaginal/cervical findings and abdominal pain were reported in the vaginal gel group, and more vaginal bleeding/spotting was reported in the vaginal ring treatment group. A summary of adverse events is presented in Table 9.

TABLE 9

Adverse Events Occurring in >1 Subject

| | Mock Cycle | |
| --- | --- | --- |
| | Vaginal Ring N = 10 | Vaginal Gel N = 11 |
| Any Adverse Event | 10 | 9 |
| Metrorrhagia | 9 | 0 |
| Dysmenorrhea | 1 | 1 |
| Cervix erythema | 1 | 1 |
| Post-procedural complication | 1 | 2 |
| Abdominal pain | 0 | 3 |
| | Embryo Transfer Cycle | |
| | Vaginal Ring N = 5 | Vaginal Gel N = 4 |
| Any Adverse Event | 5 | 3 |
| Dyspepsia | 2 | 1 |
| Nausea | 2 | 1 |
| Lower abdominal pain | 1 | 2 |
| Metrorrhagia | 3 | 1 |
| Pelvic pain | 2 | 1 |
| Upper respiratory infection | 1 | 2 |
| Headache | 1 | 2 |

There were four subjects with adverse vaginal and/or cervical findings in the mock cycle; 3 in the vaginal gel group and 1 in the intravaginal ring group. The reported vaginal/cervical adverse events for the vaginal gel subjects included cervical face ulceration, erythema, external vaginal irritation, grossly white findings, petechiae, uterine cervical erosion, and vaginal erosion with superficial peeling. The single VR patient with vaginal/cervical findings was reported to have erythema.

During the mock cycle, there was expected vaginal bleeding/spotting in both treatment groups on the day of, and up to 2 days after, the endometrial biopsy (cycle days 25-27). No subjects in the vaginal gel group reported any vaginal bleeding/spotting from cycle days 28-31, while 9 out of 10 subjects did so in the intravaginal ring group (predominantly spotting). None of the subjects in the intravaginal ring group were discontinued due to bleeding/spotting during the mock cycle. Bleeding/spotting in the intravaginal ring group occurred primarily when an intravaginal ring was used for longer than 7 days. The intravaginal ring was designed as a 7-day ring, and the second intravaginal ring was left in place for 10 days in this study to evaluate the impact of extending ring use beyond 7 days in case the ring was inadvertently left in place for longer periods of time. The vaginal spotting for the intravaginal ring group occurred either on the day or day after the intravaginal ring would normally be changed (on or after cycle day 28).

Within the intravaginal ring treatment group, there were no reports of irritation, discomfort, or issues with intercourse due to the intravaginal ring. In addition, there were no discontinuations due to the ring falling out. There were no serious adverse events, discontinuations due to a treatment-related adverse event, or reports of vaginal hemorrhage during the study.

In the embryo transfer cycle, none of the subjects had vaginal bleeding or spotting prior to the pregnancy test. Of the 5 subjects who achieved a pregnancy, 4 were using the intravaginal ring and 1 used the vaginal gel. Three of 4 had some vaginal bleeding or spotting during the pregnancy in the intravaginal ring treatment group, commencing on embryo transfer day 24-34 or at 6-7 weeks gestation. The spotting/bleeding started at the point in the pregnancy when serum progesterone levels were increasing due to production by the trophoblasts. One of the 4 pregnant intravaginal ring treatment subjects was switched to intramuscular progesterone due to an irregular bleeding pattern at 7 weeks (after embryo transfer). Two remaining women had mild spotting at 6-7 weeks which did not require any treatment. Vaginal gel subjects had no vaginal bleeding or spotting before or after pregnancy tests during the treatment period. Of note, the twin pregnancy occurred in the intravaginal ring group and this subject experienced no spotting during the pregnancy.

Example 3

The intravaginal ring of Example 1 can be used in a study to compare the efficacy of the intravaginal ring to a progesterone vaginal gel for luteal phase supplementation for in vitro fertilization. This study will be in women undergoing in vitro fertilization with fresh eggs. Multiple sites will randomize approximately 1300 eligible women in a 1:1 ratio to either a progesterone intravaginal ring or a progesterone vaginal gel once daily. Detailed past obstetrical history will be recorded, including gravidity, parity, previous abortions, and ectopic pregnancies.

The ovarian suppression/stimulation protocols will be a Lupron® (leuprolide acetate) down-regulation protocol with a combination of FSH (follicle stimulating hormone) and an LH-containing product for stimulation (luteinizing hormone). Suppression will take place during the cycle before the embryo transfer cycle. After suppression, stimulation will begin once down-regulation is achieved. The length of stimulation will be dependent upon each patient, the site's standard protocols, and/or the investigator's discretion. During stimulation, the patient will be monitored to determine when to trigger ovulation for the patient with hCG (Human Chorionic Gonadotropin). Egg retrieval will occur approximately 35-37 hours after hCG administration and embryo transfer will occur 3 or 5 days after egg retrieval. A serum pregnancy test will be conducted 2 weeks after the egg retrieval. Those patients with a βhCG <5 mIU will be discontinued from the study. Those patients with a βhCG >5 mIU will continue dosing with progesterone through 12 weeks of pregnancy, with an evaluation of clinical pregnancy rates at 8 and 12 weeks of pregnancy. All pregnancies will be followed until completion to determine live birth rates. The overall study duration will be approximately 10 months for patients who become pregnant and give birth.

In each case the patients will be administered either a progesterone intravaginal ring of Example 1 or the progesterone vaginal gel. In each case the progesterone treatment will begin the day after egg retrieval and continue through week 12 of pregnancy (10 weeks post egg retrieval).

One half of the registered participants will be administered the intravaginal ring of Example 1, which will be changed on a weekly schedule, whereby the intravaginal ring will deliver between about 10 mg of progesterone to about 30 mg of progesterone (in vivo release) to the patient each day for about seven days. Similarly, for the patients administered progesterone vaginal gel, treatment will begin the day after egg retrieval and continue through week 12 of pregnancy (10 weeks post egg retrieval).

The co-primary objectives in this study are clinical pregnancy rate (i.e., visualization of a gestational sac with fetal heart motion present on ultrasound) at 8 weeks of pregnancy (6 weeks after egg retrieval) and at 12 weeks of pregnancy (10 weeks after egg retrieval) using the intravaginal ring of Example 1 or progesterone vaginal gel to provide progesterone supplementation. In this study, pregnancy is defined as beginning 2 weeks prior to egg retrieval. Secondary objectives include a study of live birth rate, cycle cancellation rate, rate of spontaneous abortion, rate of biochemical pregnancy, rate of ectopic pregnancy, and the safety and tolerability of the intravaginal ring of Example 1.

CONCLUSION

All of the various embodiments or options described herein can be combined in any and all variations. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A method for supplementation or replacement of corpus luteal function, the method comprising administering progesterone to a subject by a monolithic intravaginal ring comprising a polysiloxane elastomer and a pharmaceutically acceptable hydrocarbon or glycerol ester of a fatty acid, or a polysiloxane elastomer and a pharmaceutically acceptable oil, in amounts that are effective to maintain a serum progesterone level of about 6 ng/mL to about 10 ng/mL over a 7-day period of use after administration to the subject;
   wherein the polysiloxane elastomer is present in an amount of about 55% to about 90% by total weight of the ring;
   wherein the pharmaceutically acceptable hydrocarbon or glycerol ester of a fatty acid or the pharmaceutically acceptable oil is present in an amount of about 1% to about 10% by total weight of the ring;
   wherein the progesterone is present in an amount of about 15% to about 30% by total weight of the ring.

2. The method of claim 1, wherein the polysiloxane elastomer is dimethylpolysiloxane elastomer.

3. The method of claim 1, wherein the polysiloxane elastomer is a dimethylpolysiloxane elastomer, and wherein the ratio by weight of progesterone to elastomer is about 1:1 to about 1:10, the progesterone is homogeneously dispersed in the elastomer, and the ratio of progesterone to hydrocarbon or glycerol esters of a fatty acid is about 1:0.1 to about 1:100.

4. The method of claim 2, wherein the intravaginal ring comprises:
   (a) about 15% to about 25% by weight of the progesterone;
   (b) about 70% to about 80% by weight of the dimethylpolysiloxane elastomer; and
   (c) about 1% to about 10% by weight of the pharmaceutically acceptable hydrocarbon or glycerol esters of a fatty acid or the pharmaceutically acceptable oil,
   wherein the progesterone is homogeneously dispersed in the elastomer.

5. The method of claim 1, wherein the intravaginal ring releases progesterone at a steady rate over a 7-day period of use.

6. The method of claim 1, wherein the intravaginal ring releases about 11 mg to about 15 mg progesterone per day at a steady state rate over a 7-day period of use.

7. The method of claim 1, wherein the pharmaceutically acceptable oil is mineral oil.

8. The method of claim 1, wherein the intravaginal ring comprises the progesterone, the dimethylpolysiloxane elastomer, and the pharmaceutically acceptable oil, in a ratio by weight of about 4:15:1, respectively, wherein the progesterone is homogeneously dispersed in the elastomer.

9. A method for treating a luteal phase defect or supporting embryo implantation and early pregnancy in a patient in need thereof, the method comprising administering progesterone to a vaginal and/or urogenital tract of a subject, in amounts that are effective to maintain a serum progesterone level of about 6 ng/mL to about 10 ng/mL over a 7-day period of use, wherein said progesterone is administered by a monolithic intravaginal ring comprising a polysiloxane elastomer and a pharmaceutically acceptable hydrocarbon or glycerol ester of a fatty acid or a polysiloxane elastomer and a pharmaceutically acceptable oil, wherein:
   the polysiloxane elastomer is present in an amount of about 55% to about 90% by total weight of the ring;
   the pharmaceutically acceptable hydrocarbon or glycerol ester of a fatty acid or the pharmaceutically acceptable oil is present in an amount of about 1% to about 10% by total weight of the ring; and
   the progesterone is present in an amount of about 15% to about 30% by total weight of the ring.

10. The method according to claim 1, said method further comprising replacing the monolithic intravaginal ring about 7 days after administration to the subject.

11. The method according to claim 1, wherein the subject is a woman with progesterone deficiency.

12. The method of claim 2, wherein the intravaginal ring consists of:
   (a) about 15% to about 25% by weight of the progesterone;
   (b) about 70% to about 80% by weight of the dimethylpolysiloxane elastomer; and
   (c) about 1% to about 10% by weight of the pharmaceutically acceptable hydrocarbon or glycerol esters of a fatty acid or the pharmaceutically acceptable oil,
   wherein the progesterone is homogeneously dispersed in the elastomer.

* * * * *